(12) United States Patent
Biondi et al.

(10) Patent No.: US 12,318,591 B2
(45) Date of Patent: *Jun. 3, 2025

(54) INJECTION MONITORING DEVICE

(71) Applicant: Genentech, Inc., South San Francisco, CA (US)

(72) Inventors: Sherri Biondi, Menlo Park, CA (US); Geraint Davies, Basel (CH); Steven N. Roe, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 250 days.

This patent is subject to a terminal disclaimer.

(21) Appl. No.: 18/066,790

(22) Filed: Dec. 15, 2022

(65) Prior Publication Data

US 2023/0181839 A1 Jun. 15, 2023

Related U.S. Application Data

(63) Continuation of application No. 16/457,555, filed on Jun. 28, 2019, now Pat. No. 11,541,187, which is a continuation of application No. PCT/US2017/068477, filed on Dec. 27, 2017.

(60) Provisional application No. 62/439,838, filed on Dec. 28, 2016.

(51) Int. Cl.
 *A61M 5/315* (2006.01)
(52) U.S. Cl.
 CPC ... *A61M 5/3157* (2013.01); *A61M 2205/3306* (2013.01); *A61M 2205/3317* (2013.01); *A61M 2205/3368* (2013.01); *A61M 2205/3584* (2013.01); *A61M 2205/3592* (2013.01); *A61M 2205/52* (2013.01); *A61M 2205/581* (2013.01); *A61M 2205/582* (2013.01); *A61M 2205/583* (2013.01); *A61M 2205/587* (2013.01); *A61M 2205/60* (2013.01); *A61M 2205/8212* (2013.01)

(58) Field of Classification Search
None
See application file for complete search history.

(56) References Cited

U.S. PATENT DOCUMENTS

| 11,173,244 B2 | 11/2021 | Agard et al. | |
| 11,541,187 B2 * | 1/2023 | Biondi | A61M 5/3137 |
| 2006/0264778 A1 | 11/2006 | Lim et al. | |

(Continued)

FOREIGN PATENT DOCUMENTS

| CN | 101438327 A | 5/2009 |
| CN | 101616705 A | 12/2009 |

(Continued)

*Primary Examiner* — Manuel A Mendez
(74) *Attorney, Agent, or Firm* — Shay Glenn LLP

(57) ABSTRACT

Drug delivery systems, devices and methods of use for recording a drug dose completion signal in a data management system are provided. Aspects of the invention include drug delivery systems comprising a syringe stopper rod that comprises a sensor component comprising a wireless transmitter module and an activation component configured to activate the sensor component when the syringe stopper rod has completed a delivery stroke, wherein the wireless transmitter module is configured to transmit a report comprising a drug dose completion signal when the sensor component is activated.

25 Claims, 14 Drawing Sheets

(56) References Cited

U.S. PATENT DOCUMENTS

| | | | |
|---|---|---|---|
| 2008/0306443 A1* | 12/2008 | Neer | A61M 5/007 604/121 |
| 2011/0313395 A1 | 12/2011 | Krulevitch et al. | |
| 2016/0030683 A1 | 2/2016 | Taylor et al. | |
| 2020/0206424 A1 | 7/2020 | Rios et al. | |

FOREIGN PATENT DOCUMENTS

| | | |
|---|---|---|
| CN | 102149416 A | 8/2011 |
| CN | 203710476 U | 7/2014 |
| CN | 105705184 A | 6/2016 |
| CN | 105764549 A | 7/2016 |
| JP | 2001517496 A | 10/2001 |
| WO | WO2014/116987 A1 | 7/2014 |
| WO | WO2015/187793 A1 | 12/2015 |
| WO | WO2016/078863 A1 | 5/2016 |
| WO | WO2016/087512 A1 | 6/2016 |
| WO | WO2016/110592 A1 | 7/2016 |
| WO | WO2016/118736 A1 | 7/2016 |
| WO | WO2016/128207 A1 | 8/2016 |
| WO | WO2017/070391 A2 | 4/2017 |
| WO | WO2018/111969 A1 | 6/2018 |

* cited by examiner

A.

B.

INJECTION MONITORING DEVICE

CROSS REFERENCE TO RELATED APPLICATIONS

This application is a continuation of U.S. application Ser. No. 16/457,555, filed Jun. 28, 2019, which is a continuation of International Application No. PCT/US2017/068477, filed Dec. 27, 2017, which claims the benefit of U.S. Provisional Application No. 62/439,838, filed Dec. 28, 2016, each of which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

The present invention relates to drug delivery systems and methods of use thereof for recording administration of a drug dose to a subject. Aspects of the invention include a syringe stopper rod comprising a sensor component that is configured to transmit a report comprising a drug dose completion signal to a data management component, e.g., a mobile computing device.

BACKGROUND

The effectiveness of a medication for the treatment of a given disease or disorder is highly dependent on patient adherence to a defined dosage regimen. A typical dosage regimen may require a patient to receive a medication according to a specific schedule, e.g., two doses per day for a period of several days, weeks or months. The ability of a patient to successfully follow a specified dosage regimen is therefore of paramount importance to the ultimate efficacy of the medication in treating the disease or disorder.

In spite of its importance, patient compliance with a dosage regimen remains a challenge, especially for medications that are self-administered. A patient's non-compliance with a dosage regimen can stem from any number of factors, including, for example, failing to correctly administer the proper dose of the medication, forgetting to administer the medication at a designated time, or failing to record and/or remember the time and date of a previous administration, and therefore failing to correctly determine the time and date at which a subsequent administration should take place. Additionally, a patient may be uncertain as to whether a given lot of a medication has expired, whether the medication has reached a proper temperature for administration following its removal from cold storage, or how much of the medication to administer at a designated time. Furthermore, proper recordation of each medication dose delivered to the patient, as well as additional information relating to the medication itself (e.g., the temperature of the drug at the time of administration) is important to various other parties, including, e.g., health care providers, pharmacies, and drug manufacturers.

As provided herein, aspects of the present invention provide drug delivery systems and methods of use that embody certain advantageous alternatives to existing drug delivery devices and methods, and which address one or more of the needs described above.

SUMMARY OF THE DISCLOSURE

Drug delivery systems and methods of use for recording a drug dose completion signal in a data management system are provided. Aspects of the invention include drug delivery systems comprising a syringe stopper rod that comprises a sensor component comprising a wireless transmitter module and an activation component configured to activate the sensor component when the syringe stopper rod has completed a delivery stroke, wherein the wireless transmitter module is configured to transmit a report comprising a drug dose completion signal when the sensor component is activated. In some embodiments, a subject drug delivery system comprises a housing, a drug reservoir, a drug delivery cannula, an actuation component, and a data management component that is configured to receive and record a report that is transmitted from the sensor component. Aspects of the invention further include methods of using the subject drug delivery systems and devices to record administration of a drug dose to a patient.

Aspects of the invention include syringe stopper rods comprising: a sensor component comprising a wireless transmitter module; and an activation component configured to activate the sensor component when the syringe stopper rod has completed a delivery stroke; wherein the wireless transmitter module is configured to transmit a report comprising a drug dose completion signal when the sensor component is activated. In some embodiments, the sensor comprises a circuit board component. In some embodiments, the circuit board component comprises a contact switch. In some embodiments, the contact switch is a momentary contact switch. In some embodiments, the contact switch is a non-momentary contact switch. In some embodiments, the circuit board component comprises a position sensor. In some embodiments, the circuit board component comprises a force sensor. In some embodiments, the sensor component comprises a power component. In some embodiments, the power component comprises a battery. In some embodiments, the sensor component is mounted on a proximal end of the syringe stopper rod and comprises a thumb pad. In some embodiments, the thumb pad is removably coupled to the proximal end of the syringe stopper rod. In some embodiments, the activation component is located at a proximal end of the syringe stopper rod. In some embodiments, the activation component comprises an activation cam, and is configured to activate the sensor component when the activation cam contacts a proximal end of the syringe. In some embodiments, the activation component further comprises a switch key.

In some embodiments, a syringe stopper rod further comprises a sensor housing configured to house the sensor component, wherein the sensor housing comprises one or more openings configured to allow the activation component to mechanically contact the sensor component when the activation cam contacts the proximal end of the syringe, thereby activating the sensor component. In some embodiments, the activation component is located at a distal end of the syringe stopper rod. In some embodiments, the activation component is configured to activate the sensor component when a syringe stopper contacts a distal end of the syringe. In some embodiments, the activation component comprises an internal rod. In some embodiments, the internal rod comprises one or more detent snaps that are configured to shift a position of the internal rod with respect to the syringe stopper rod when the syringe stopper contacts the distal end of the syringe, thereby activating the sensor component.

In some embodiments, a syringe stopper rod further comprises an indicator component. In some embodiments, the indicator component is configured to indicate a ready state to a user. In some embodiments, the indicator component is configured to indicate an unready state to a user. In some embodiments, the indicator component is configured to indicate a dose-in-progress state to a user. In some embodiments, the indicator component is configured to indicate a dose completed state to a user. In some embodiments, the indicator component is configured to indicate a sleep mode to a user. In some embodiments, the indicator component is configured to indicate a low battery state to a user. In some embodiments, the indicator component is a visual indicator component. In some embodiments, the visual indicator component comprises a light-emitting component. In some embodiments, the light-emitting component comprises a light-emitting diode (LED). In some embodiments, the light-emitting component comprises an organic light-emitting diode (OLED). In some embodiments, a syringe stopper rod further comprises a light pipe. In some embodiments, a syringe stopper rod further comprises a light pipe diffuser.

In some embodiments, the indicator component is a haptic indicator component. In some embodiments, the haptic indicator component comprises a vibration component. In some embodiments, the indicator component is an auditory indicator component. In some embodiments, the auditory indicator component is configured to produce a plurality of unique sounds. In some embodiments, the sensor component further comprises a light sensor. In some embodiments, a syringe stopper rod further comprises a sensor housing configured to house the sensor component, wherein the sensor housing comprises a window that is configured to allow ambient light to contact the light sensor. In some embodiments, the sensor component further comprises a motion sensor. In some embodiments, the sensor component further comprises a touch sensor. In some embodiments, a syringe stopper rod further comprises a capacitance sensor component that is configured to detect a skin contact from a user. In some embodiments, the capacitance sensor component is located on an outer surface of the syringe stopper rod. In some embodiments, the syringe stopper rod comprises a thumb pad, and the capacitance sensor component is located on an outer surface of the thumb pad. In some embodiments, the sensor component further comprises a temperature sensor. In some embodiments, the sensor component comprises a non-volatile memory component. In some embodiments, the non-volatile memory component comprises at least one drug identification characteristic. In some embodiments, the at least one drug identification characteristic is encoded into the non-volatile memory component of the sensor.

In some embodiments, at least one drug identification characteristic is encoded into a non-volatile memory component on a drug reservoir, and the sensor component is configured to transfer the at least one drug identification characteristic from the non-volatile memory component on the drug reservoir to the non-volatile memory component on the sensor. In some embodiments, the sensor component is configured to wirelessly transfer the at least one drug identification characteristic from the non-volatile memory component on the drug reservoir to the non-volatile memory component on the sensor. In some embodiments, the at least one drug identification characteristic is selected from the group consisting of: a drug name, a drug concentration, a drug dose, a drug dosage, a serial number, a lot number, an expiration date, a manufacturing site, or any combination thereof. In some embodiments, a distal end of the syringe stopper rod comprises a coupler component that is configured to mechanically couple the syringe stopper rod to a syringe stopper. In some embodiments, the coupler component comprises a threaded coupler component, an adhesive couple component, a snap fit coupler component, a magnetic coupler, or any combination thereof.

Aspects of the invention include drug delivery systems comprising: a housing; a drug reservoir; a drug delivery cannula; an actuation component comprising: a sensor component comprising a wireless transmitter module; and an activation component configured to activate the sensor component when the actuation component has completed a delivery stroke; wherein the wireless transmitter module is configured to transmit a report comprising a drug dose completion signal when the sensor component is activated; and a data management component configured to receive and record the report from the sensor component. In some embodiments, the sensor comprises a non-volatile memory component that is encoded with at least one drug identification characteristic. In some embodiments, the drug reservoir comprises a non-volatile memory component that is encoded with at least one drug identification characteristic. In some embodiments, the sensor is configured to acquire the at least one drug identification characteristic from the non-volatile memory component on the drug reservoir. In some embodiments, the at least one drug identification characteristic is selected from the group consisting of: a drug name, a drug concentration, a drug dose, a drug dosage, a serial number, a lot number, an expiration date, a manufacturing site, or any combination thereof. In some embodiments, the drug reservoir comprises a syringe. In some embodiments, the syringe is a pre-filled syringe. In some embodiments, the drug reservoir comprises a vial. In some embodiments, the drug reservoir comprises a cartridge. In some embodiments, the drug reservoir is removably coupled to the housing. In some embodiments, the drug delivery cannula comprises a needle. In some embodiments, the needle is removably coupled to the housing. In some embodiments, a drug delivery system further comprises a needle shield.

In some embodiments, the drug delivery cannula comprises a catheter. In some embodiments, the catheter is an implantable catheter. In some embodiments, the actuation component is removably coupled to drug reservoir. In some embodiments, the drug reservoir comprises a syringe, and the actuation component comprises a syringe stopper rod, as described herein. In some embodiments, the drug delivery cannula comprises a needle, and the drug delivery system further comprises a needle safety device (NSD). In some embodiments, the NSD is configured to sequester the needle upon completion of a delivery stroke by the actuation component. In some embodiments, a drug delivery system further comprises a finger flange component.

In some embodiments, the data management system comprises a mobile computing device. In some embodiments, the mobile computing device is a smart phone. In some embodiments, the smart phone comprises a computer application configured to record administration of a drug dose to a patient. In some embodiments, the report comprises a drug temperature value. In some embodiments, the report comprises a dose amount. In some embodiments, the report comprises a dose administration time stamp. In some embodiments, the report comprises a geographical location. In some embodiments, the report comprises an anatomical location. In some embodiments, the report comprises a drug authentication signal. In some embodiments, the drug authentication signal comprises at least one drug identification characteristic. In some embodiments, the at least one drug identification characteristic is selected from the group consisting of: a drug name, a drug concentration, a drug dose, a drug dosage, a serial number, a lot number, an expiration date, a manufacturing site, or any combination thereof. In some embodiments, the data management component is configured to validate the drug authentication signal. In some embodiments, the data management component is configured to utilize the drug authentication signal to obtain one or more additional drug identification characteristics. In some embodiments, the one or more additional drug identification characteristics are selected from the group consisting of: a drug name, a drug concentration, a drug dose, a drug dosage, a serial number, a lot number, an expiration date, a manufacturing site, or any combination thereof.

In some embodiments, the data management component is configured to transmit the drug authentication signal to a remote database and receive the one or more additional drug identification characteristics in response. In some embodiments, the data management component is an Internet-enabled data management component, and is configured to wirelessly transmit the drug authentication signal over the Internet to a remote database, and to wirelessly receive the one or more additional drug authentication characteristics over the Internet in response.

Aspects of the invention include methods for recording administration of a drug dose to a patient, the methods comprising: inserting the drug delivery cannula of the drug delivery system, as described herein, into the patient; completing a delivery stroke of the actuation component, thereby causing the activation component to activate the sensor component, and causing the wireless transmitter module to transmit a report comprising a drug dose completion signal to the data management component; and receiving and recording the report in the data management component, thereby recording administration of the drug dose to the patient. In some embodiments, the data management system comprises a mobile computing device. In some embodiments, the mobile computing device is a smart phone. In some embodiments, the smart phone comprises a computer application configured to record administration of a drug dose to the patient.

In some embodiments, the report comprises a drug temperature value. In some embodiments, the report comprises a dose amount. In some embodiments, the report comprises a dose administration time stamp. In some embodiments, the report comprises a geographical location. In some embodiments, the report comprises an anatomical location. In some embodiments, the report comprises a drug authentication signal. In some embodiments, the drug authentication signal comprises at least one drug identification characteristic. In some embodiments, the at least one drug identification characteristic is selected from the group consisting of: a drug name, a drug concentration, a drug dose, a drug dosage, a serial number, a lot number, an expiration date, a manufacturing site, or any combination thereof.

In some embodiments, a method further comprises validating the drug authentication signal. In some embodiments, a method further comprises utilizing the drug authentication signal to obtain one or more additional drug identification characteristics. In some embodiments, the one or more additional drug identification characteristics are selected from the group consisting of: a drug name, a drug concentration, a drug dose, a drug dosage, a serial number, a lot number, an expiration date, a manufacturing site, or any combination thereof. In some embodiments, a method further comprises transmitting the drug authentication signal to a remote database and receiving the one or more additional drug identification characteristics in response. In some embodiments, the data management component is an Internet-enabled data management component, and the method comprises wirelessly transmitting the drug authentication signal over the Internet to a remote database, and wirelessly receiving the one or more additional drug authentication characteristics over the Internet in response.

Definitions

Figure 1:
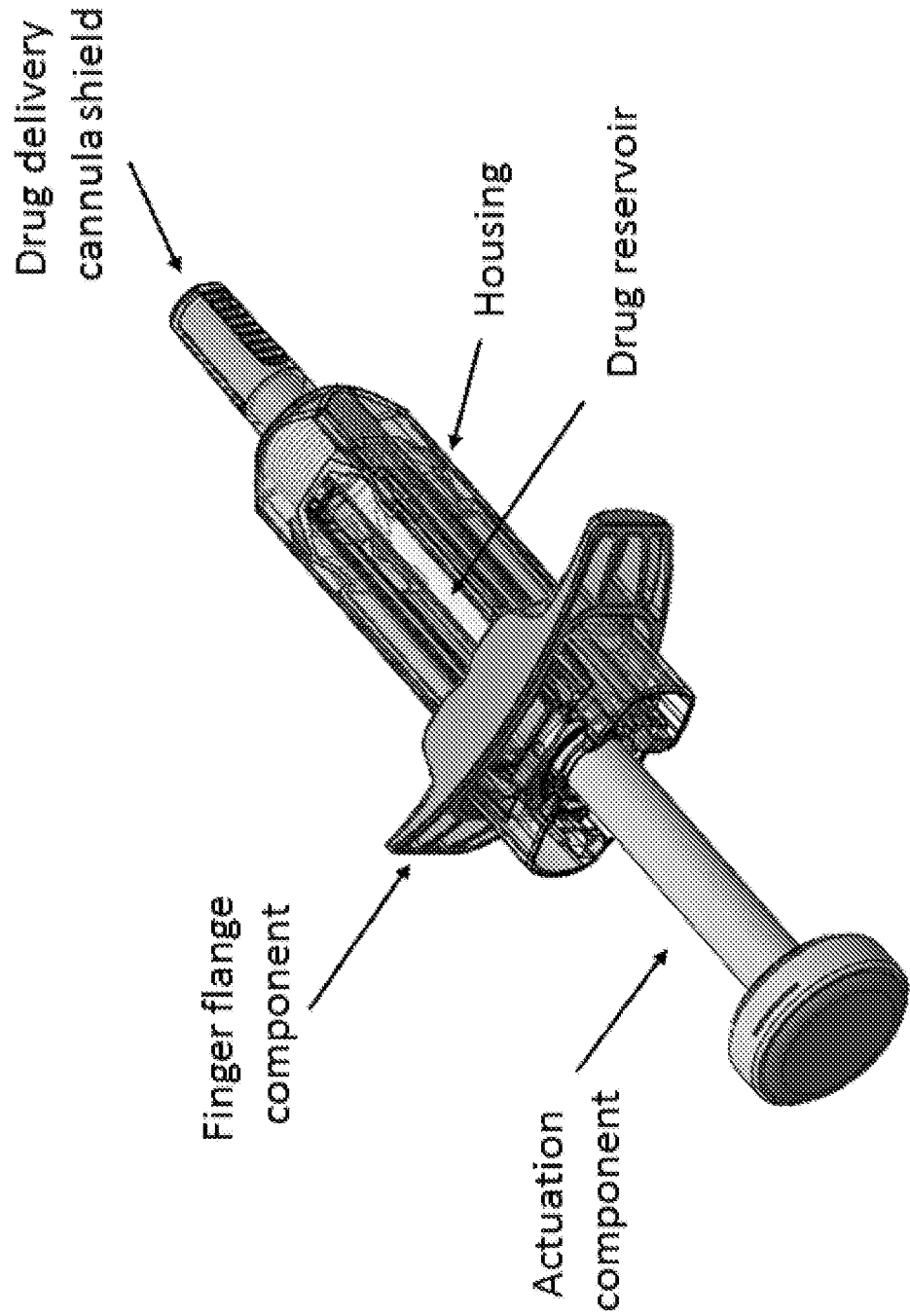
FIG. 1 is a three dimensional rendering of a drug delivery system according to one embodiment of the invention.

For purposes of interpreting this specification, the following definitions will apply, and whenever appropriate, terms used in the singular will also include the plural and vice versa.

The terms "drug", "medicine" and "medication" as used interchangeably herein refer to a substance that has a physiological effect when introduced into the body of a patient.

The term "patient" as used herein refers to a human or a non-human animal who is being treated and/or monitored for a medical condition or disorder.

The term "delivery stroke" as used herein refers to a physical motion of an actuation component of a subject drug delivery system or device that results in the dispensation of a specified dose of a drug.

The terms "dose" and "drug dose" as used interchangeably herein refer to an amount of a drug to be administered to a patient at any one time. A "dose" can be a volume-based dose (e.g., a specific volume of a drug to be administered at one time) or a weight-based dose (e.g., a specific weight of a drug to be administered at one time).

The terms "dosage" and "drug dosage" as used interchangeably herein refer to the frequency at which a drug dose is to be administered to a patient.

The term "cam" as used herein refers to a projection that extends from a movable mechanical member (e.g., a projection that extends from a syringe stopper rod).

The term "switch key" as used herein refers to a component that is configured to align and transfer the motion of a mechanical element through one or more openings or windows in a housing so as to translate the motion of the mechanical element through the housing.

The term "detent snap" as used herein refers to mechanical element that prevents motion until it is released, displaced, or dislodged.

The term "detent notch" as used herein refers to a depression in which a detent snap is configured to remain until it is released, displaced, or dislodged.

The term "haptic indicator" as used herein refers to a component that creates a signal that is detectable via a patient's or a user's sense of touch.

The term "drug identification characteristic" as used herein refers to any information relating to a drug's identity and/or its biochemical characteristics (including, but not limited to, a drug's name, concentration, dose, dosage, serial number, lot number, expiration date, manufacturing date, site of manufacture, or any combination thereof).

The term "cannula" as used herein refers to a thin, tube-like element that is configured to be inserted into the body of a patient (e.g., inserted into an artery or a vein, or inserted subcutaneously). As used herein, a "cannula" can be rigid, semi-rigid, or flexible.

The term "catheter" as used herein refers to a thin, flexible tube-like element that is configured to be inserted into the body of a patient (e.g., inserted into an artery or a vein, or inserted subcutaneously).

The terms "smart phone" and "smartphone" as used interchangeably herein refer to a mobile phone with an operating system that comprises features of a personal computer operating system (e.g., the ability to install and run application programs, the ability to send and receive data).

The terms "graphical user interface" or "GUI" as used interchangeably herein refer to a user interface that is configured to allow a user to interact with an electronic device (e.g., a data management component) through one or more graphical icons and/or text-based commands.

The term "time stamp" as used herein refers to a specific date and time that are associated with an event, indicating the specific date and time when the event took place.

The term "Internet-enabled" as used herein refers to the ability of the referenced device or system to send and/or receive information over the Internet.

DETAILED DESCRIPTION

Drug delivery systems and methods of use for recording a drug dose completion signal in a data management system are provided. Aspects of the invention include drug delivery systems comprising a syringe stopper rod that comprises a sensor component comprising a wireless transmitter module and an activation component configured to activate the sensor component when the syringe stopper rod has completed a delivery stroke, wherein the wireless transmitter module is configured to transmit a report comprising a drug dose completion signal when the sensor component is activated. In some embodiments, a subject drug delivery system comprises a housing, a drug reservoir, a drug delivery cannula, an actuation component, and a data management component that is configured to receive and record a report that is transmitted from the sensor component. Aspects of the invention further include methods of using the subject drug delivery systems and devices to record administration of a drug dose to a patient.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "the component" includes reference to one or more components, and so forth. It is further noted that the claims may be drafted to exclude any optional element. As such, this statement is intended to serve as antecedent basis for use of such exclusive terminology as "solely." "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Systems and Devices:

As reviewed above, aspects of the invention include systems and devices thereof configured to transmit a report comprising a drug dose completion signal upon completion of a delivery stroke. In some embodiments, a subject system comprises a housing, a drug reservoir, a drug delivery cannula, an actuation component comprising a sensor component comprising a wireless transmitter module, and an activation component that is configured to activate the sensor component when the actuation component has completed a delivery stroke, wherein the wireless transmitter module is configured to transmit a report comprising a drug dose completion signal when the sensor component is activated, and a data management component configured to receive and record the report from the sensor component. Each of these components is now further described in greater detail.

Sensor Component:

As reviewed above, aspects of the invention include systems and devices that comprise a sensor component. Sensor components in accordance with embodiments of the invention are configured to acquire one or more data inputs from the subject systems and devices, or from the immediate vicinity of the subject systems and devices, and to transmit a report comprising a drug dose completion signal in response to activation of the sensor component by an activation component. In certain embodiments, the report transmitted by the sensor component includes additional information, such as, e.g., one or more drug identification characteristics (described further herein).

In some embodiments, a sensor component comprises a circuit board component that is configured or adapted to mechanically support and electrically connect one or more electronic components of a subject sensor. Circuit board components in accordance with embodiments of the invention can include, without limitation, printed circuit boards, etched circuit boards, flexible circuit boards, or any combination thereof. In some embodiments, a circuit board component comprises a printed circuit board (PCB).

Circuit board components in accordance with embodiments of the invention can comprise conductive tracks, pads, or other features that are etched from conductive sheets (e.g., copper sheets) that are attached to a non-conductive substrate. In certain embodiments, standard circuit components, such as, e.g., capacitors, resistors, memory components, and the like, are electrically connected to a circuit board component (e.g., are soldered to a PCB). Connection of one or more electronic circuit components to a PCB results in a printed circuit assembly (PCA) or a printed circuit board assembly (PCBA), which terms are used interchangeably herein.

Aspects of the invention include switches that are configured to establish or break an electrical contact in a subject circuit board component in response to an external stimulus (e.g., in response to an external mechanical stimulus). In some embodiments, a circuit board component comprises a momentary contact switch that is configured to establish or break an electrical contact only while the momentary contact switch is in an activated state. In some embodiments, a circuit board component comprises a non-momentary contact switch that is configured to establish or break an electrical contact until the non-momentary switch is activated again. In some embodiments, establishing or breaking an electrical contact in a subject circuit board component in response to an external stimulus is used as a trigger mechanism to initiate a procedure by a sensor component (e.g., is used to initiate transmission of a report comprising a drug dose completion signal by the sensor component).

In some embodiments, a sensor component comprises a position sensor that is configured or adapted to permit position measurement of one or more components of the subject drug delivery systems and devices. For example, in some embodiments, a position sensor is configured to detect and/or measure a position of an actuation component. In some embodiments, a position sensor is configured to detect an orientation of one or more components of a subject device (e.g., an orientation of a drug delivery cannula). Position sensors in accordance with embodiments of the invention can be absolute position sensors or relative position sensors, and can be linear, angular or multi-axis position sensors. In some embodiments, a position sensor is configured to acquire a plurality of measurements over a defined time interval, or during execution of a drug delivery procedure, in order to measure a position of one more components of the subject systems or devices, either as a function of time, or as a function of progression through the drug delivery procedure.

In some embodiments, a sensor component comprises a force sensor that is configured or adapted to detect and/or measure one or more forces in one or more components of the subject drug delivery systems and devices. For example, in some embodiments, a force sensor is configured to measure the amount of force that is applied to a drug reservoir by an actuation component (e.g., the amount of force that is applied to a syringe stopper by a syringe stopper rod). Force sensors in accordance with embodiments of the invention can be absolute or relative force sensors.

In some embodiments, a sensor component comprises a light sensor that is configured or adapted to detect and/or measure ambient light. For example, in some embodiments, a light sensor is configured to determine whether an amount of ambient light in the vicinity of a subject drug delivery system or device is above a predetermined threshold value. Light sensors in accordance with embodiments of the invention can be absolute or relative light sensors. In some embodiments, a light sensor is used to detect an increase in ambient light, thereby indicating that a subject device has been removed from its packaging, removed from a storage container, and/or removed from a dark location.

In some embodiments, a sensor component comprises a motion sensor that is configured or adapted to detect and/or measure motion of a subject drug delivery system or device. For example, in some embodiments, a motion sensor is configured to determine whether a device, or component thereof, moves more than a predetermined threshold value. Motion sensors in accordance with embodiments of the invention can be absolute or relative motion sensors. In some embodiments, a motion sensor is used to detect motion of a subject device, thereby indicating that a user has begun interacting with the device.

In some embodiments, a sensor component comprises a temperature sensor that is configured or adapted to detect and/or measure a temperature of one or more components of the subject systems or devices. For example, in some embodiments, a temperature sensor is configured to determine whether the temperature of a drug in a drug reservoir is above a predetermined threshold value, or is within a predetermined temperature range. Temperature sensors in accordance with embodiments of the invention can be absolute or relative temperature sensors. In some embodiments, a temperature sensor is used to detect an increase in temperature, thereby indicating that a subject device has been removed from cold storage and has reached a temperature that is suitable for administration of the drug to a patient.

In some embodiments, a sensor component comprises a touch sensor that is configured or adapted to detect and/or measure contact by an object that is conductive, or that has a dielectric value that is different from air. In some embodiments, a touch sensor comprises one or more detection components (e.g., capacitive sensing components) that are placed on an external surface of a subject drug delivery system or device (e.g., on a thumb pad of a subject syringe stopper rod) and are electrically connected to the touch sensor. When a user touches a detection component, an electrical signal is sent to the touch sensor, indicating that the user has touched the device. In some embodiments, a touch sensor is used to determine that a user has made physical contact with a subject device (e.g., that a portion of a user's skin has made physical contact with a subject device), thereby indicating that the user has begun interacting with the device.

Aspects of the subject sensor components include a power component that is configured or adapted to provide electrical power to the sensor component. In some embodiments, a power component comprises a battery. In some embodiments, a power component comprises a rechargeable battery. In some embodiments, a power component comprises one or more standard electrical cords that are configured to supply electrical power to a sensor component by establishing electrical contact with an external power source (e.g., a standard electrical outlet). In some embodiments, a subject system or device comprises an on/off switch or button that can be used to turn power to the system or device on or off, as desired.

In some embodiments, a sensor component comprises a memory component that is configured or adapted to store one or more drug identification characteristics therein. Memory components in accordance with embodiments of the invention can be volatile or non-volatile memory components. In some embodiments, a memory component is encoded with one or more drug identification characteristics before it is connected to the sensor component (e.g., the memory component is encoded with one or more drug identification characteristics at the time the memory component is manufactured). In some embodiments, a memory component is encoded with one or more drug identification characteristics after the memory component has been connected to the sensor component. In certain embodiments, a sensor component comprises a data acquisition component that is configured to acquire the one or more drug identification characteristics that are stored in the memory component from an external source (e.g., from an external encoder, or from a memory component on a drug reservoir). In some embodiments, a memory component is configured to wirelessly receive encoded information (e.g., a data acquisition component is configured to wirelessly acquire the one or more drug identification characteristics). In some embodiments, a sensor component comprises a near-field communication (NFC) component and/or a radio frequency identification (RFID) component that are configured for data exchange.

Drug identification characteristics in accordance with embodiments of the invention broadly include any information relating to a drug's identity and/or its biochemical characteristics (including, but not limited to, a drug's name, concentration, dose, dosage, serial number, lot number, expiration date, manufacturing date, site of manufacture, or any combination thereof). In some embodiments, a memory component can further comprise one or more patient identification characteristics (including, but not limited to: a patient name, patient identification number, prescription number, demographic information, patient group or subgroup, or any combination thereof). In some embodiments, a memory component can further comprise one or more drug delivery device identification characteristics (including, but not limited to: a system or device name, type, model number, serial number, lot number, date of manufacture, place of manufacture, or any combination thereof).

Aspects of the subject sensor components include a wireless transmitter module that is configured to wirelessly transmit data to a networked device (e.g., a data management component). In some embodiments, a wireless transmitter module is configured to communicate with one or more networked devices using a wireless transmission component (e.g., a communication link that utilizes, e.g., infrared light, radio-frequency, or optical waves). Networked devices in accordance with embodiments of the invention broadly include any device or component that communicates with at least one other device over a communication link. Non-limiting examples of networked devices include mobile computing devices (e.g., smart phones, laptop computers) that use, e.g., Bluetooth, Bluetooth low energy (BLE), or Wi-Fi connections. In some embodiments, a wireless transmitter module is configured to wirelessly communicate directly with a network or directly with a remote computing device (i.e., without first communicating with a mobile computing device). In certain embodiments, a wireless transmitter module comprises an antenna.

Sensor components in accordance with embodiments of the invention are configured to transmit a report comprising a drug dose completion signal when the sensor component is activated by an activation component. In some embodiments, a drug dose completion signal comprises an indication that an actuation component has completed a delivery stroke. In some embodiments, a data management component is configured to determine a volume of drug that was delivered to the patient by identifying the drug delivery system or device, and determining the volume of drug that is administered in a single delivery stroke of the identified system or device. In some embodiments, a data management component is encoded with information relating to the volume of a drug that is administered in a single delivery stroke of a specified system or device.

In some embodiments, a subject sensor component is configured or adapted to determine one or more operational states of a drug delivery system or device. For example, in some embodiments, a sensor component is configured to determine a ready state, wherein the system or device is ready to administer a drug dose to the patient. In some embodiments, a sensor component is configured to determine an unready state, wherein the system or device is not ready to administer a drug dose to the patient. In some embodiments, a sensor component is configured to determine a dose-in-progress state, wherein the system or device is actively administering a drug dose to the patient. In some embodiments, a subject system or device can be configured to administer a drug dose to a patient over a time frame that ranges from about 1 second up to about 30 minutes, such as about 5, 10, 15, 20, 25, 30, 35, 40, 45, 50, 55, or 60 seconds, or about 1, 2, 3, 4, 5, 6, 7, 8, 9 or 10 minutes or more, such as about 11, 12, 13, 14, 15, 16, 17, 18, 19, 20, 21, 22, 23, 24, 25, 26, 27, 28 or 29 minutes or more. In some embodiments, a subject system or device is configured to remain in a dose-in-progress operational state for a period of time that is equal to the time frame for administering the drug to the patient.

In some embodiments, a sensor component is configured to determine a sleep mode state (e.g., a low power state), wherein the system or device is operating in reduced power mode, and is not ready to administer a drug dose to the patient. In some embodiments, a sensor component is configured to determine a low battery state, wherein the battery charge is below a predetermined level.

Determination of any of the states described herein can be accomplished by analysis of one or more inputs from one or more of the subject sensor components. For example, in some embodiments, a ready state can be determined when a temperature value from a temperature sensor falls within a predetermined range (i.e., indicating that the drug is at a desired temperature range for administration) and a position sensor indicates that the system or device is in a desired position or orientation for administration (e.g., a position of an actuation component is determined to be correct for administration of the drug to the patient).

In some embodiments, a sensor component can communicate a determined operational state, as described above, to another component of the system or device (e.g., to a data management component). In certain embodiments, the data management component can then indicate the operational state to a user (e.g., on a GUI), thereby communicating the operational state to the user. In some embodiments, as described further herein, the subject systems and devices can comprise one or more indicator components that are configured to communicate an operational state of the system or device to a user (e.g., a "ready to inject" operational state).

Sensor components in accordance with embodiments of the invention can be mounted in any suitable location on the subject systems or devices. For example, in some embodiments, a sensor component can be mounted in a housing that is positioned anywhere on the system or device. In one embodiment, a sensor component is mounted in a thumb pad that is attached to an actuation component (e.g., a syringe stopper rod, as described further herein). In some embodiments, a sensor component is configured to be removably coupled to subject drug delivery system or device. For example, in some embodiments, a sensor component is mounted in a thumb pad, and the thumb pad is configured to be removably coupled to a proximal end of a syringe stopper rod. In some embodiments, a sensor component can be mounted in a finger flange component. In certain embodiments, a sensor component is formed into a single unit. In certain embodiments, a sensor component comprises two or more individual units (e.g., two or more different PCBAs) that are electrically connected to one another, each of which is mounted in a suitable location on a subject drug delivery system or device.

Figure 2:
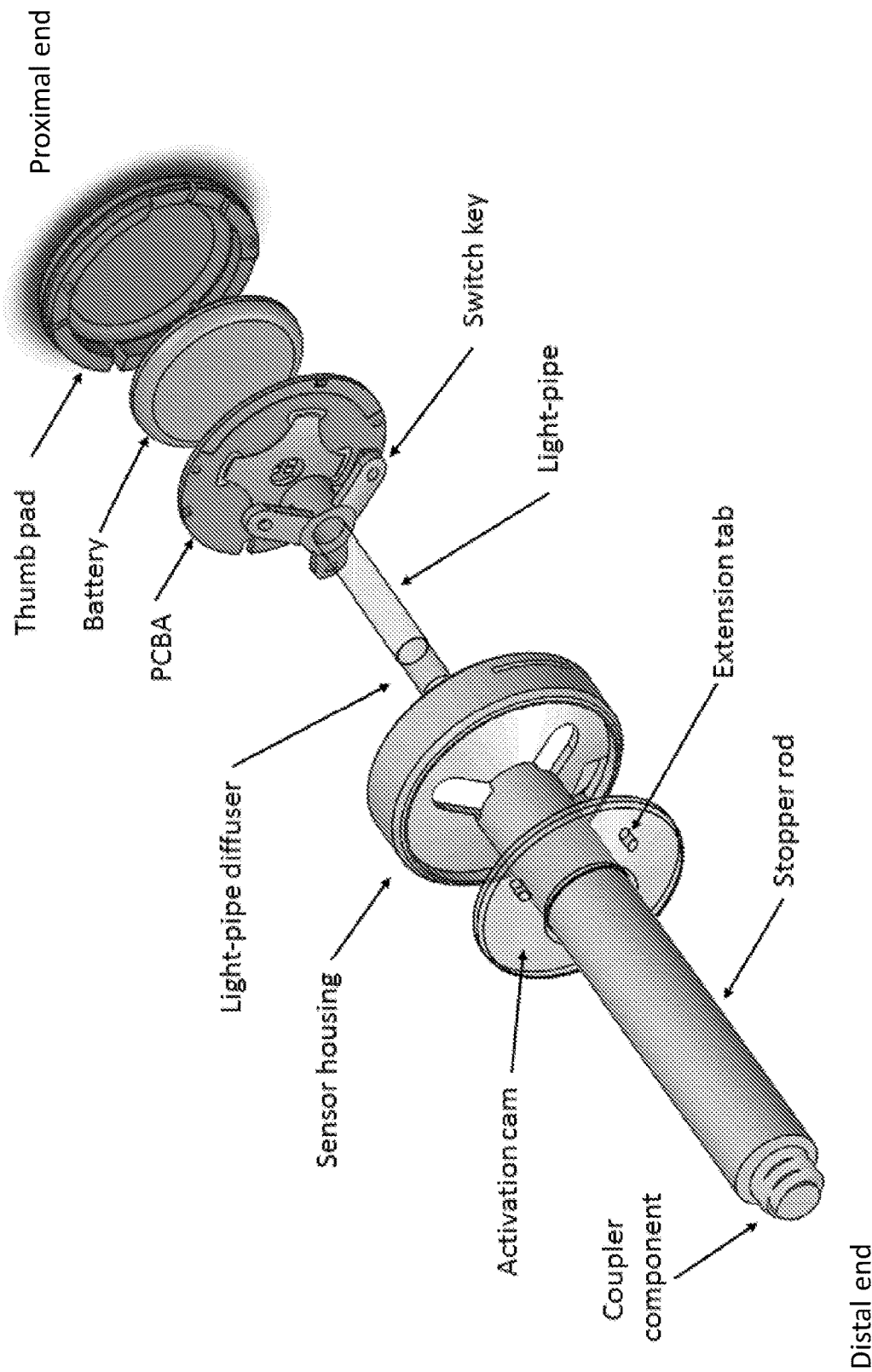
FIG. 2 is a three dimensional exploded view of a syringe stopper rod according to one embodiment of the invention.
Figure 3:
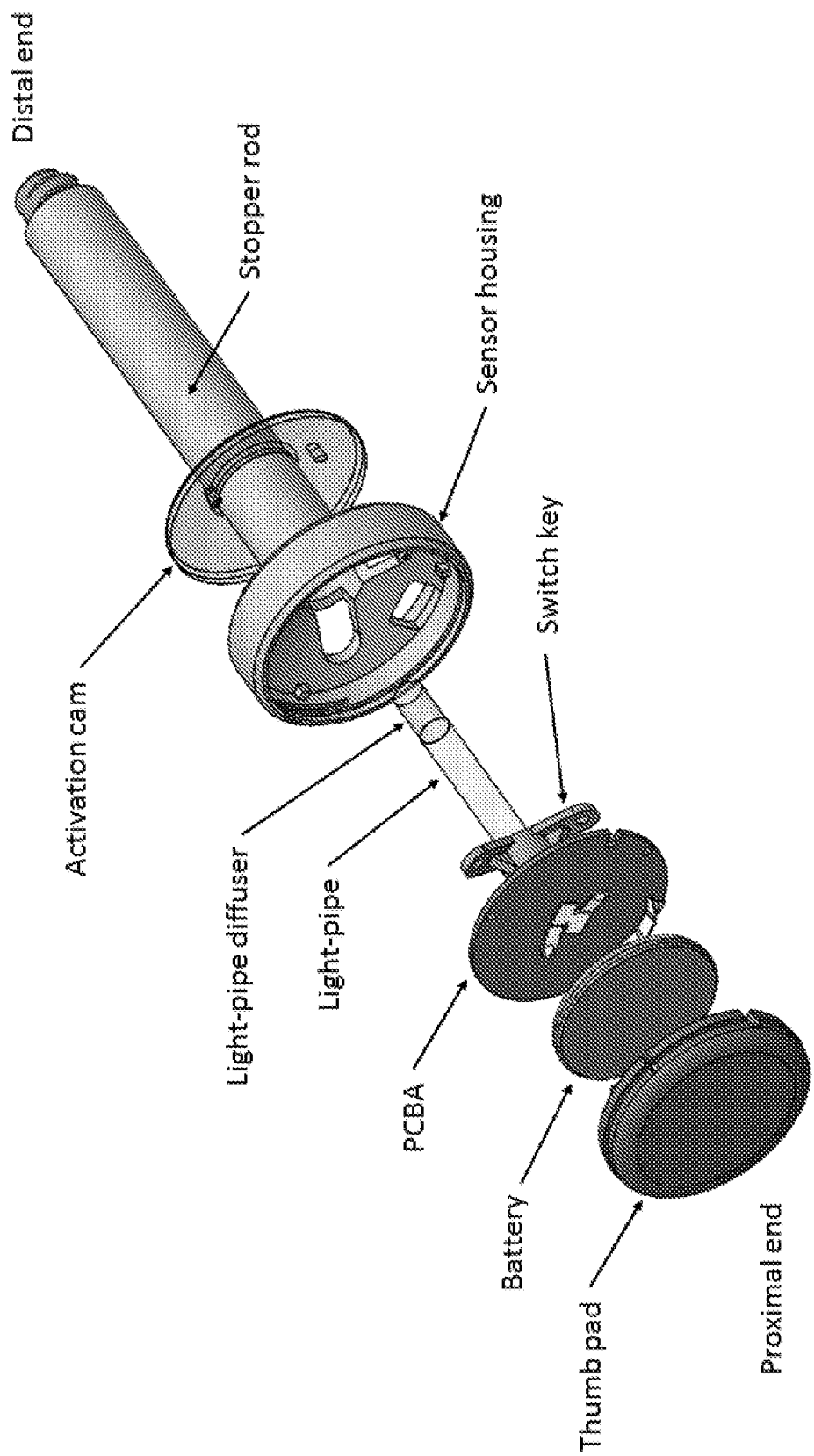
FIG. 3 is a three dimensional exploded view of a syringe stopper rod according to one embodiment of the invention.
Figure 4:
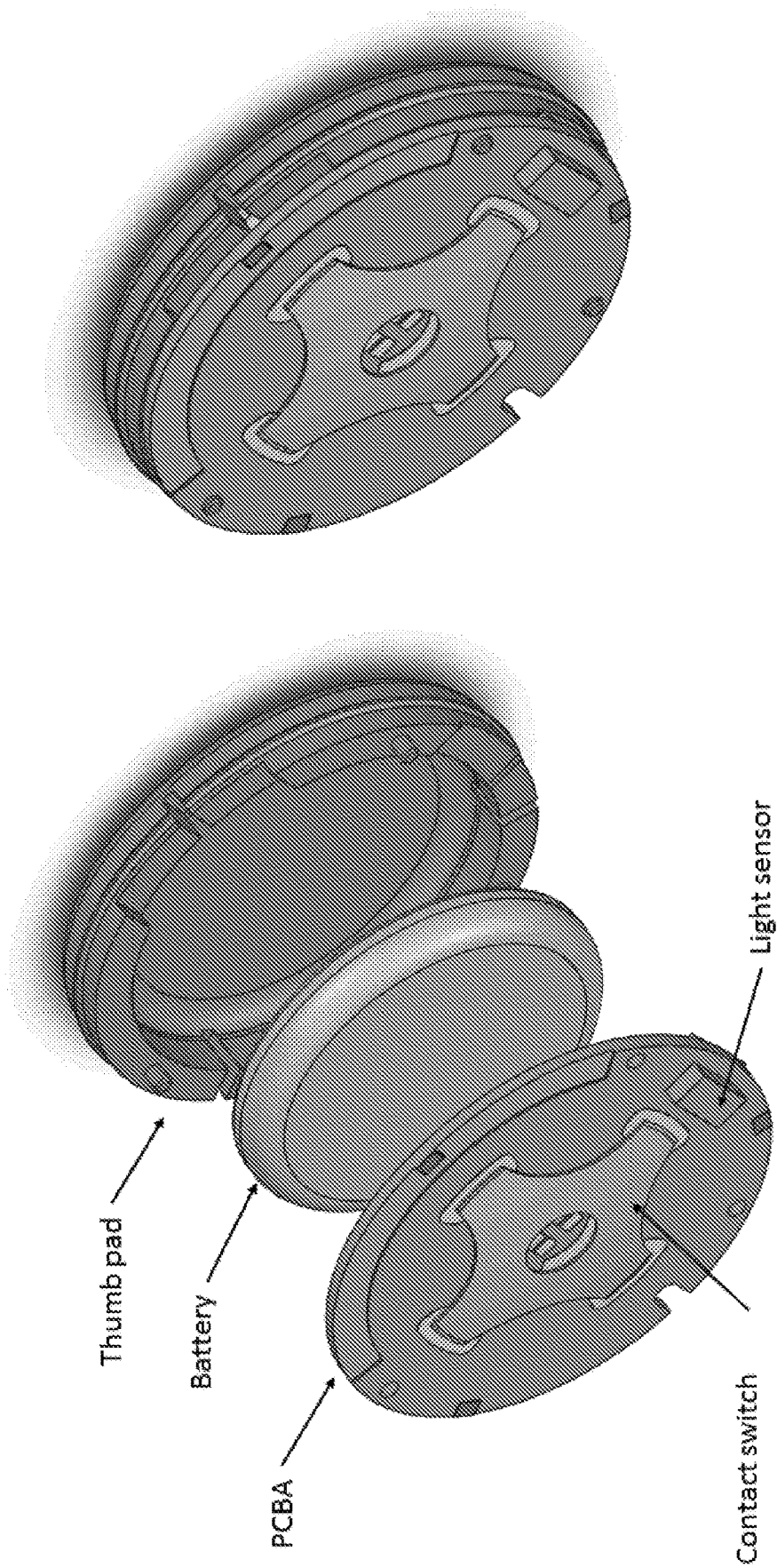
FIG. 4 is a three dimensional exploded view and a three dimension assembled view of a sensor component according to one embodiment of the invention.
Figure 5:
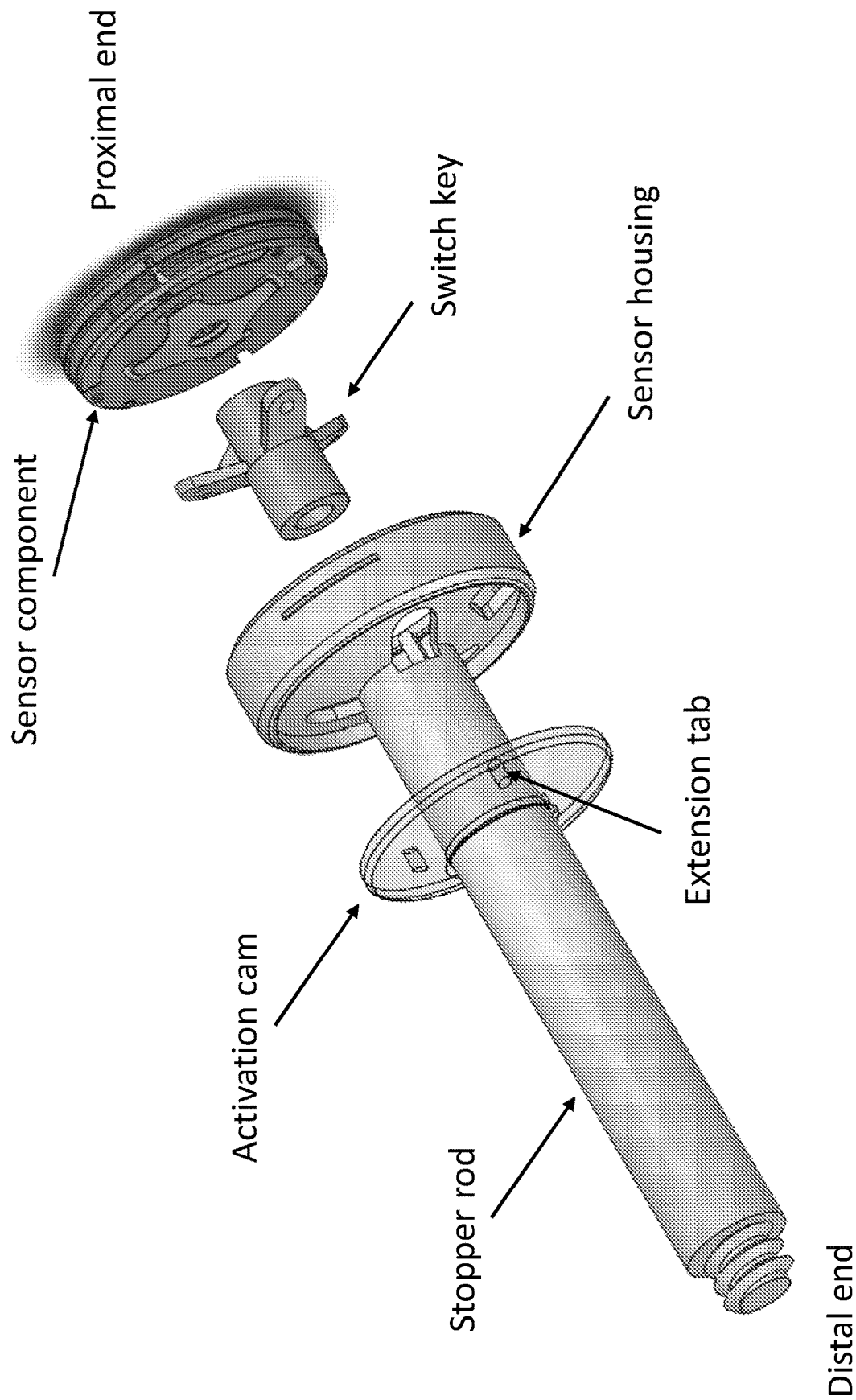
FIG. 5 is a three dimensional exploded view of a syringe stopper rod according to one embodiment of the invention.
Figure 6:
FIG. 6 is a three dimensional assembled view of a syringe stopper rod according to one embodiment of the invention.
Figure 10:
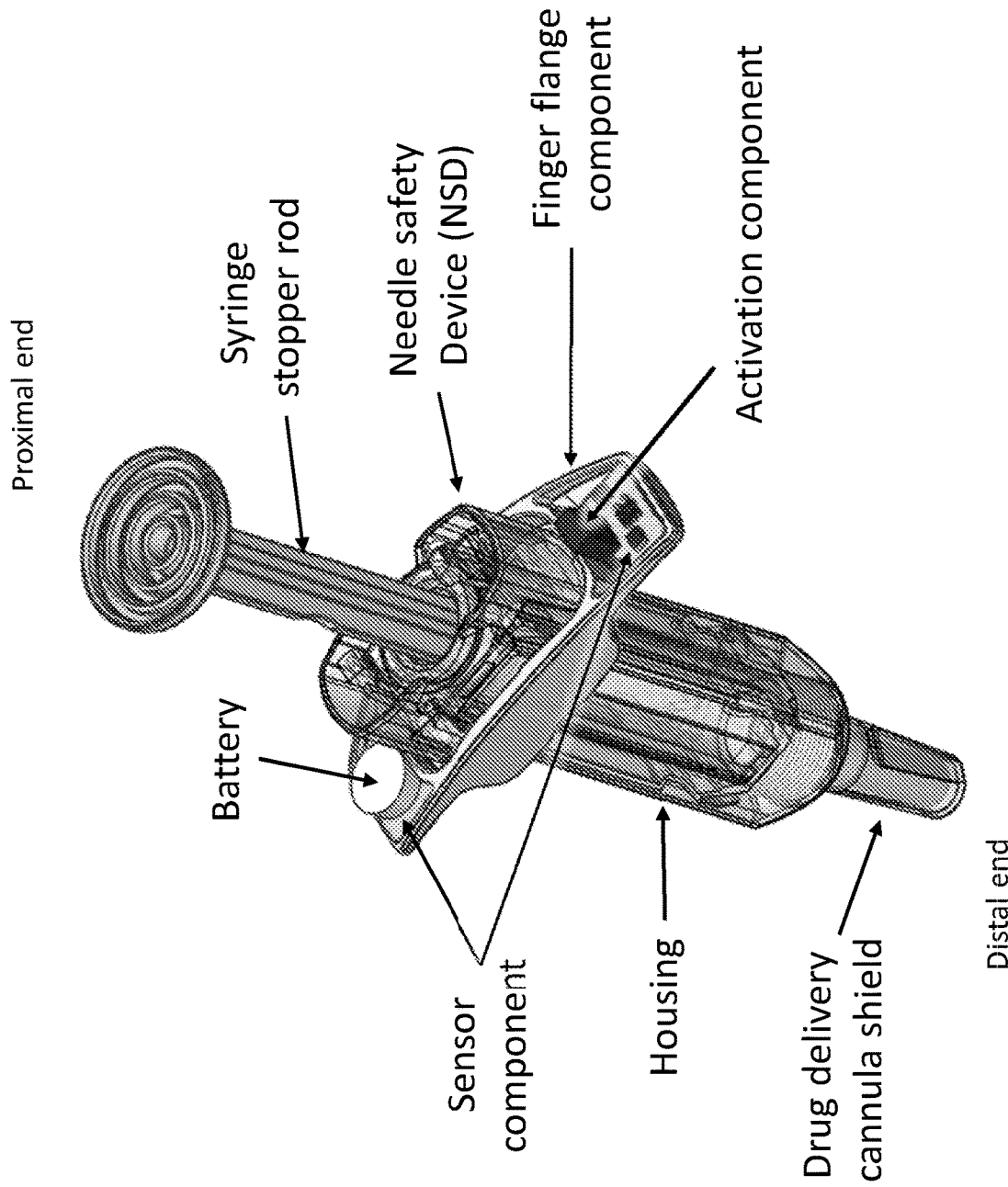
FIG. 10 is a three dimensional rendering of a drug delivery system according to one embodiment of the invention
Figure 11:
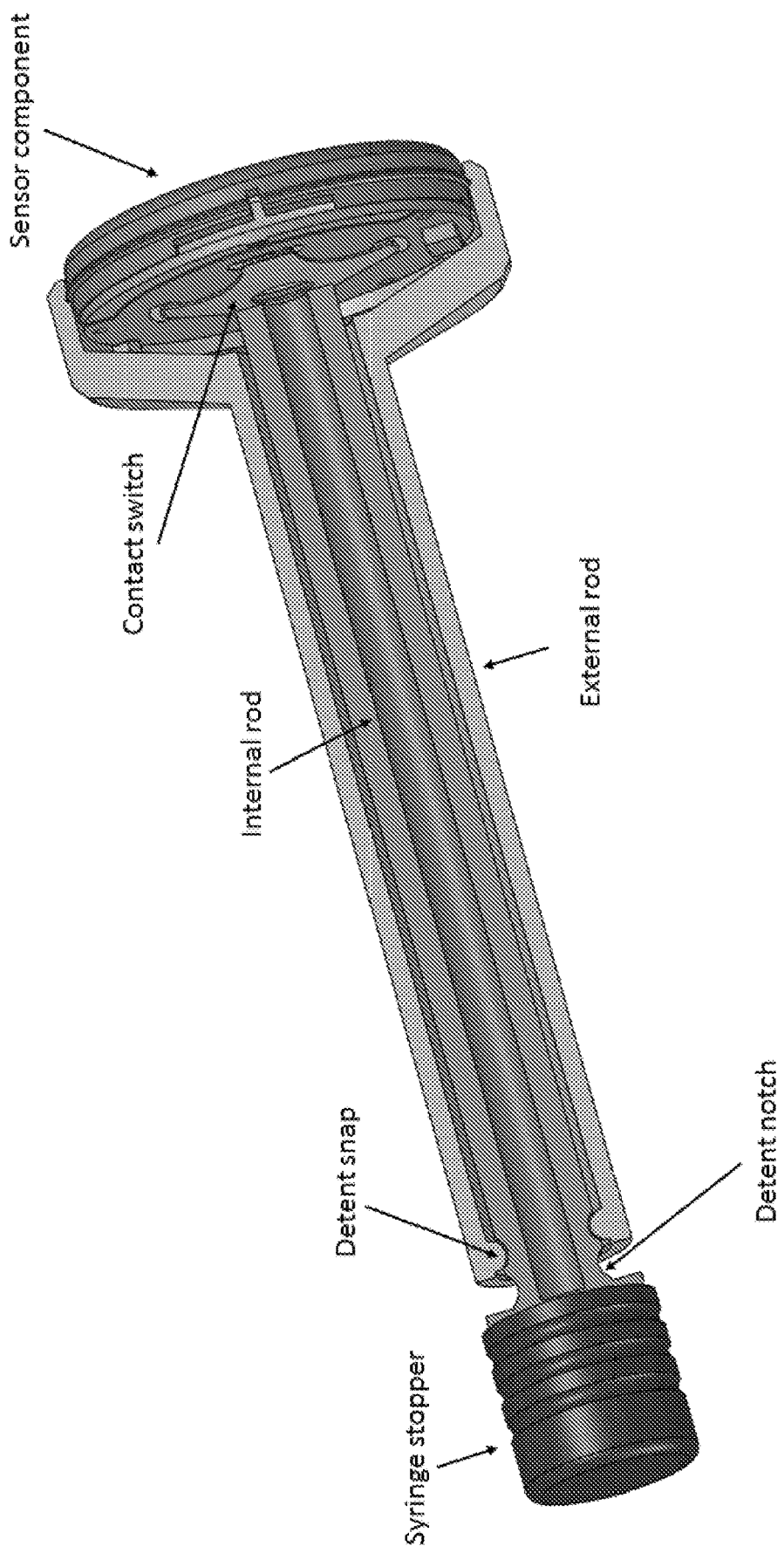
FIG. 11 is a three dimensional assembled view with an exposed cross sectional view of a syringe stopper rod according to one embodiment of the invention.
Figure 12:
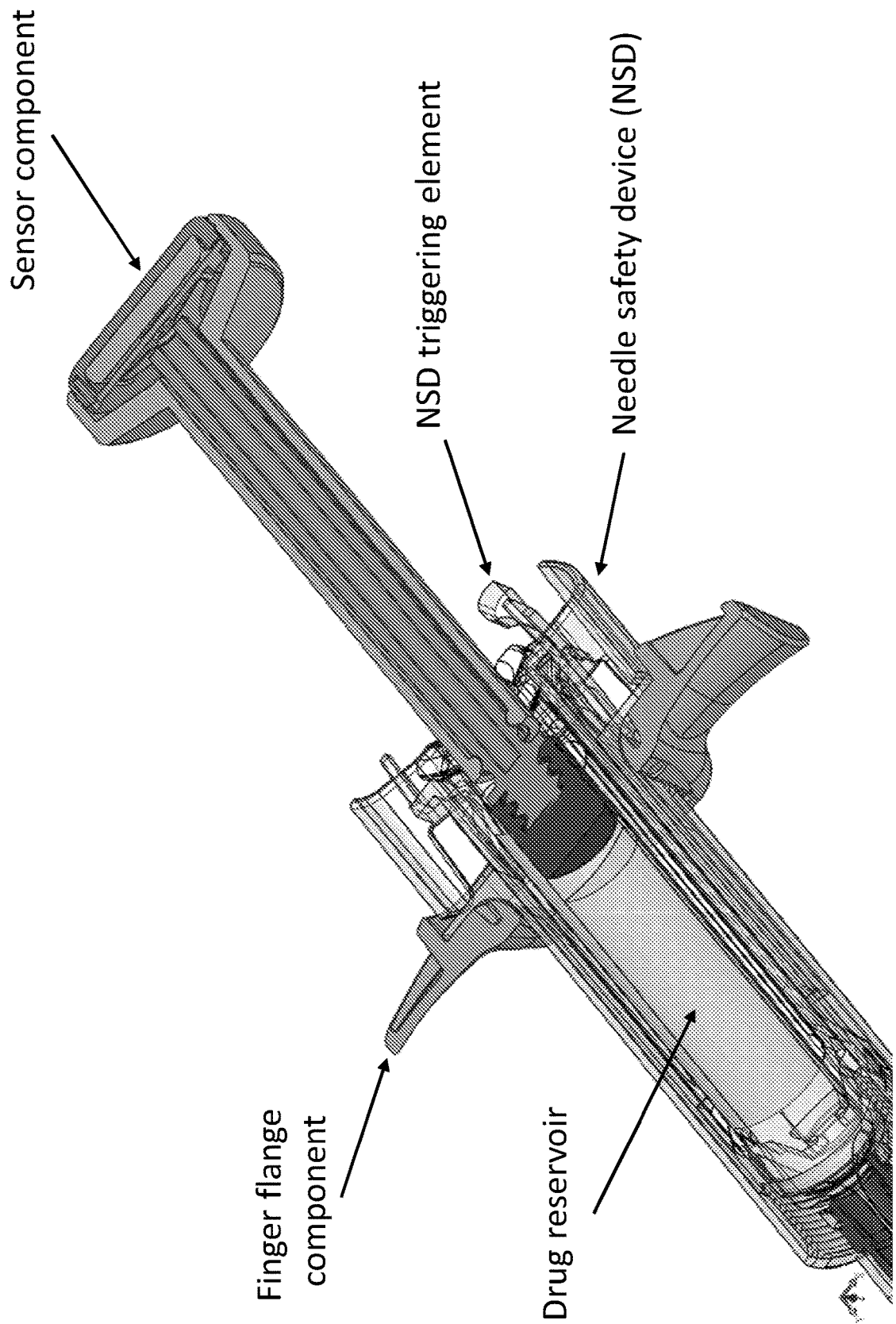
FIG. 12 is a three dimensional assembled view with an exposed cross sectional view of a drug delivery system according to one embodiment of the invention.
Figure 13:
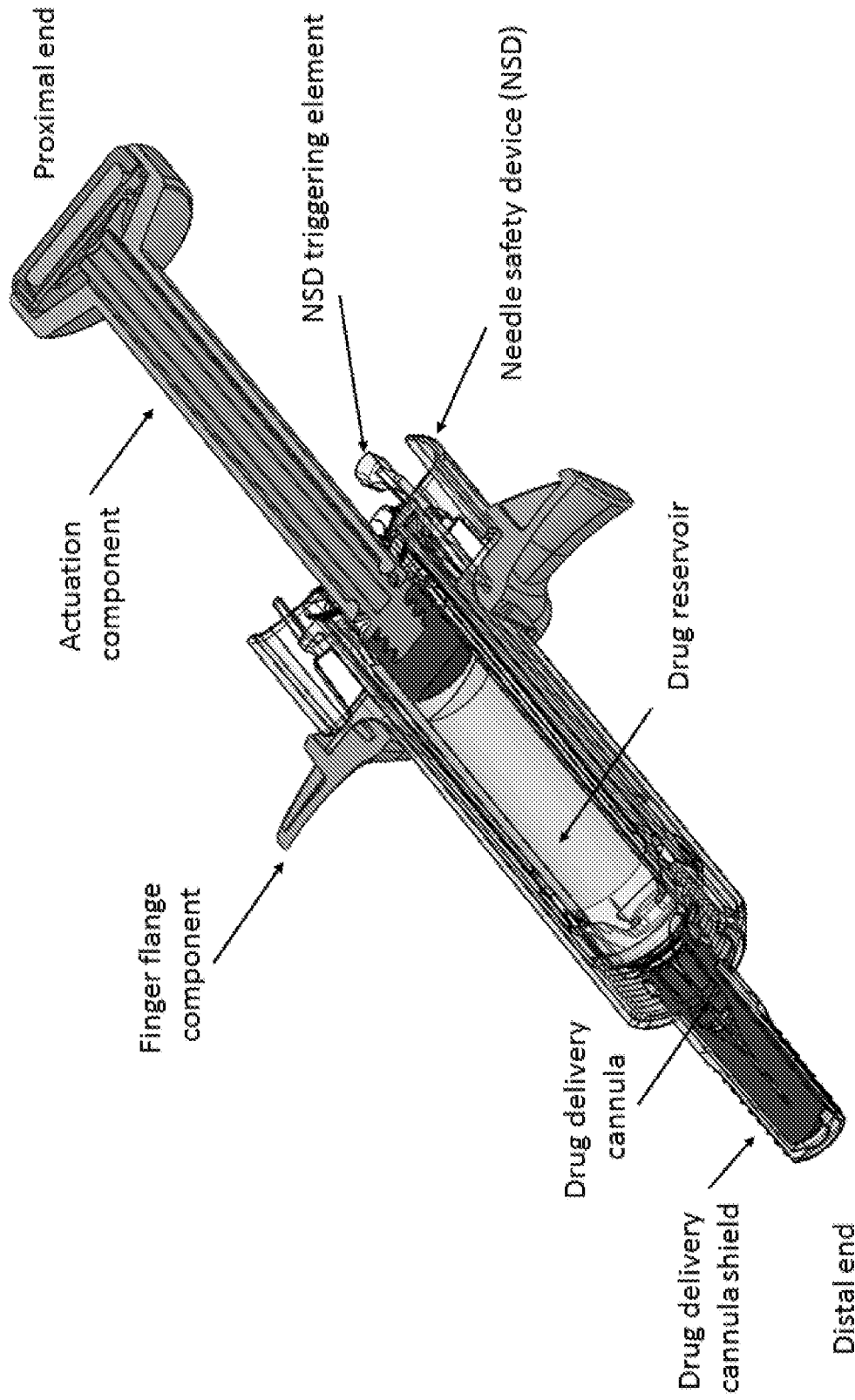
FIG. 13 is a three dimensional assembled view with an exposed cross sectional view of a drug delivery system according to one embodiment of the invention.

Turning now to FIG. 2, a sensor component is depicted, comprising a PCBA and a battery. The depicted sensor component is configured to fit within a sensor housing that is located at a proximal end of the depicted syringe stopper rod. FIG. 3 provides another view of a sensor component that comprises a PCBA and a battery, and which is configured to fit within a sensor housing that is located at a proximal end of the depicted syringe stopper rod. FIG. 4 provides an exploded view of a sensor component that comprises a PCBA and a battery. The depicted sensor component comprises a light sensor and a contact switch that are mounted on the PCBA. The depicted sensor component is configured to fit together with a thumb pad component to form a disc-shaped sensor unit, which in some embodiments can be removably coupled to a subject drug delivery system or device. FIG. 5 shows an exploded view of a syringe stopper rod that comprises a disc-shaped sensor unit at the proximal end. In the depicted embodiment, the disc-shaped sensor unit is configured to fit within a sensor housing located at the proximal end of the syringe stopper rod. FIG. 6 shows an assembled view of syringe stopper rod wherein the sensor component has been inserted into the sensor housing at the proximal end of the syringe stopper rod. FIG. 10 shows an assembled view of one embodiment of a subject drug delivery system, wherein the sensor component comprises two individual units, which are each located in a finger flange component. FIGS. 11-13 show an assembled view of one embodiment of a subject drug delivery system, wherein the sensor component is located in a sensor housing at the proximal end of the syringe stopper rod.

Activation Component:

Aspects of the invention include an activation component that is configured to mechanically interact with a sensor component (e.g., a momentary contact switch on a sensor component) when an actuation component has completed a delivery stroke. By relying on a mechanical interaction between an activation component and the sensor component, the subject drug delivery systems and devices provide improved accuracy and reliability regarding their ability to detect successful completion of a delivery stroke of an actuation component. The subject drug delivery systems and devices are configured to transmit a report comprising a drug dose completion signal only when a suitable mechanical interaction has taken place between an activation component and a sensor component. As such, the subject drug delivery systems and devices avoid the shortcomings of other drug delivery systems and devices that rely on electronic perception of a delivery stroke by, e.g., one or more electronic components, such as motion sensors or position sensors, which can malfunction, or fail to accurately perceive or detect the completion of a delivery stroke by an actuation component.

Activation components in accordance with embodiments of the invention can be positioned in any suitable location on the subject systems or devices so that they can mechanically interact with a contact switch upon completion of a delivery stroke by an actuation component. In some embodiments, an activation component is located at a proximal end of an actuation component (e.g., a syringe stopper rod) and is configured to mechanically interact with a contact switch when the actuation component arrives at a specified distal location, thereby completing a delivery stroke. In some embodiments, an activation component is configured to activate a contact switch when the activation component makes physical contact with a portion of a subject system or device. For example, in some embodiments, an actuation component comprises a syringe stopper rod having an activation component at the proximal end, and the activation component is configured to activate a contact switch when the proximal end of the syringe stopper rod makes contact with the proximal end of the syringe barrel.

In some embodiments, an activation component comprises a plurality of individual components that work in concert to activate a contact switch. For example, in one embodiment, an activation component comprises an activation cam that makes contact with a portion of a system or device (e.g., makes contact with a proximal end of a syringe barrel) and a switch key that transfers the physical contact through one or more openings in the sensor housing to activate the contact switch. In some embodiments, an activation cam comprises a plurality of extension tabs that extend from the activation cam to the switch key, and that transfer the physical contact from the activation cam to the switch key.

Turning now to FIG. 2, a three dimensional exploded view of a syringe stopper rod is depicted. In the depicted embodiment, the activation cam is mounted on a distal face of the sensor housing and comprises a plurality of extension tabs that are configured to pass through a plurality of openings in the sensor housing to contact the switch key. When the extension tabs contact the switch key, the contact switch on the sensor component is activated.

In some embodiments, an activation component is located at a distal end of an actuation component (e.g., a syringe stopper rod) and is configured to mechanically interact with a contact switch when the actuation component arrives at a specified distal location, thereby completing a delivery stroke. For example, in some embodiments, an actuation component comprises a syringe stopper rod having an activation component at the distal end, and the activation component is configured to activate a contact switch when the distal end of the syringe stopper rod makes contact with the distal end of the syringe barrel.

In some embodiments, an activation component comprises a plurality of individual components that work in concert to activate a contact switch. For example, in one embodiment, an activation component comprises an internal rod that extends from the distal end of a syringe stopper rod to a location that is close to a proximal end of the syringe stopper rod, and comprises a plurality of detect notches at its distal end. The detent notches are configured to mechanically interact with one or more detent snaps that are located on the distal end of the syringe stopper rod. When the syringe stopper makes contact with the distal end of the syringe barrel, thereby completing a delivery stroke, the generated force causes the detent snaps to move from one detent notch position to another, in the distal direction. As a result, the internal rod shifts its position with respect to the external rod element, causing the proximal end of the internal rod element to physically interact with the contact switch on the sensor component. Any suitable configuration of detent notches and detent snaps can be utilized in accordance with embodiments of the invention. For example, in some embodiments, an activation component can include one or more detent notches at its proximal end, which are configured to mechanically interact with one or more detent snaps that are located on the proximal end of the syringe stopper rod. In some embodiments, an activation component can include one or more detent notches that are centrally located on the activation component, which are configured to mechanically interact with one or more detent snaps that are centrally located on the syringe stopper rod.

Turning now to FIG. 10, a three dimensional assembled view of a drug delivery system is depicted. The depicted system comprises a sensor component that comprises two individual units that are electrically connected to one another, each or which is mounted in a finger flange component. The depicted embodiment further comprises an activation component that is mounted on one of the sensor units, and which is configured to be activated when the needle safety device is triggered.

Turning now to FIG. 11, a three dimensional assembled view of a syringe stopper rod with an exposed cross section is depicted. The depicted embodiment has a sensor component at the proximal end, and is configured to couple to a syringe stopper at the distal end. The depicted embodiment has an internal rod element that has a plurality of detent notches at the distal end, and an external rod element that has a plurality of detent snaps. When the detent snaps shift position in the distal direction from a first detent notch to a second detent notch, the internal rod shifts its position with respect to the external rod, thereby activating the contact switch.

Figure 14:
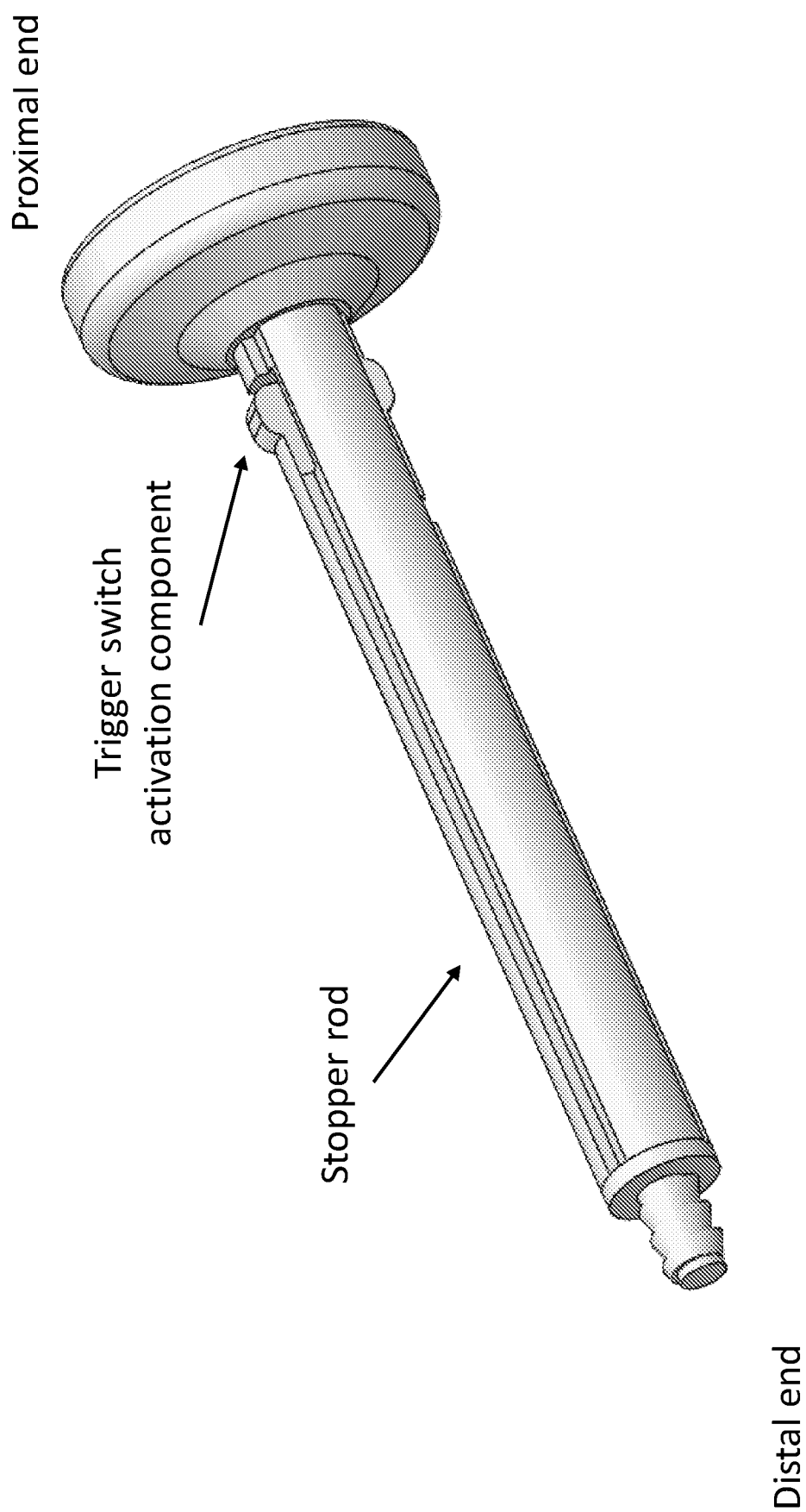
FIG. 14 is a three dimensional rendering of a syringe stopper rod according to one embodiment of the invention.

Turning now to FIG. 14, a three dimensional view of a syringe stopper rod with a trigger switch activation component is depicted. The depicted embodiment has a trigger switch activation component that is located near the proximal end of the syringe stopper rod. During a delivery stroke, the trigger switch activation component is deflected in an inward direction as the proximal portion of the syringe stopper enters the syringe barrel. After deflecting inward at the end of the delivery stroke, the trigger switch activates a contact switch (not shown) disposed inside the syringe stopper rod, thereby activating the sensor component (also not shown).

Actuation Component:

Aspects of the invention include actuation components that are configured to move, thereby causing a drug to be dispensed from the drug reservoir and injected into the patient. Actuation components in accordance with embodiments of the invention can generally be actuated by any suitable mechanism. In some embodiments, an actuation component is configured to be moved manually by a user. In some embodiments, an actuation component is configured to be moved automatically by one or more driver components (e.g., one or more mechanical, electrical, or electromechanical controllers). In certain embodiments, a subject drug delivery system or device in configured to automatically inject a drug dose into the patient, and is characterized as an autoinjector.

In some embodiments, an actuation component can include a controller that is coupled to one or more assemblies or subassemblies of the subject systems or devices. The controller can be configured or adapted (e.g., programmed, if the controller comprises an electrical or electromechanical component) to move the actuation component in response to a user input or an activation signal.

In some embodiments, an actuation component can comprise one or more coupling components that are configured or adapted to mechanically connect the actuation component to one or more additional components of the subject systems or devices. Coupling components in accordance with embodiments of the invention broadly include threaded couplers, adhesive couplers, snap-fit couplers, magnetic couplers, or any combination thereof. For example, in one embodiment, an actuation component comprises a syringe stopper rod that comprises a threaded coupler located at the distal end. The threaded coupler is configured to screw into a proximal end of a syringe stopper to physically couple the syringe stopper rod to the syringe stopper.

Figure 8:
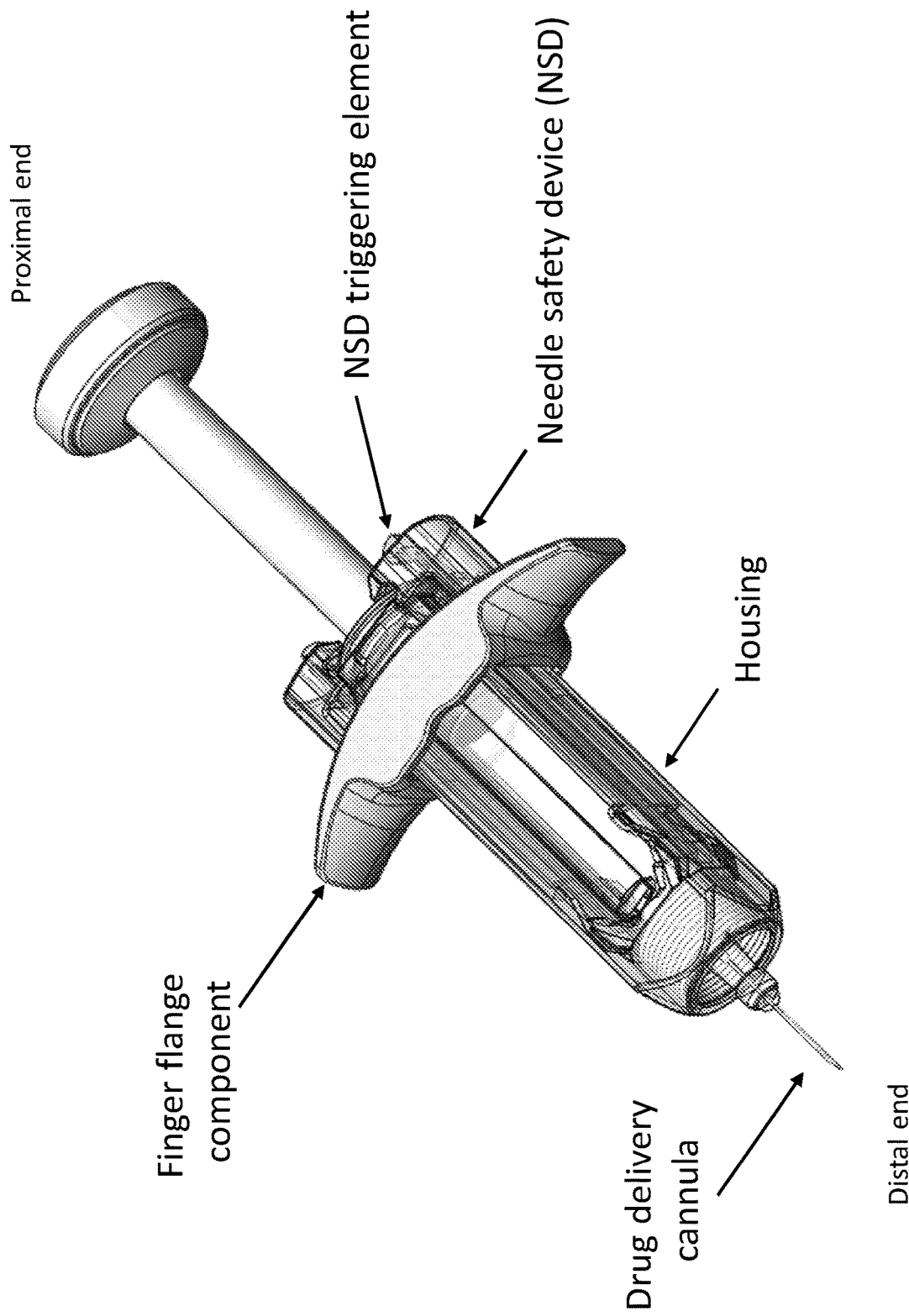
FIG. 8 is a three dimensional rendering of a drug delivery system according to one embodiment of the invention.
Figure 9:
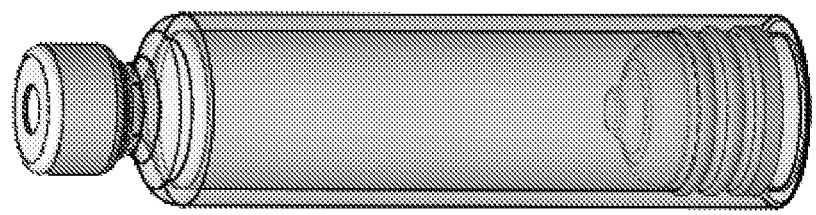
FIG. 9, Panel A is a three dimensional rendering of a drug cartridge according to one embodiment of the invention. Panel B is three dimensional rendering of a vial according to one embodiment of the invention.
Figure 9:
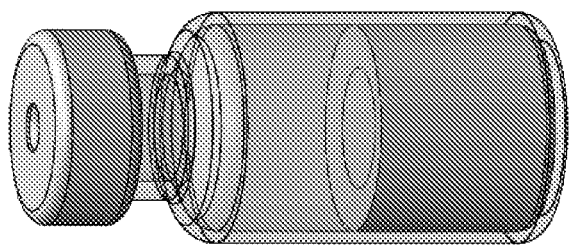

FIG. 1 provides two different views of a drug delivery device in accordance with embodiments of the invention, comprising an actuation component in the form of a syringe stopper rod. FIG. 2 depicts an actuation component that comprises a threaded coupler component for attachment to a syringe stopper. FIG. 11 depicts an actuation component that comprises a syringe stopper attached to a syringe stopper rod. FIGS. 8-9 show the actuation component depicted in FIG. 11 positioned within a drug delivery system in accordance with embodiments of the invention.

Indicator Component:

Aspects of the invention include indicator components that are configured or adapted to communicate one or more operational states of the subject drug delivery systems or devices to a user. In use, a given operational state of a subject drug delivery system or device can be assigned a specific indicator signal, and the subject indicator components can be used to communicate the specific indicator signal to a user, thereby indicating to the user that the system or device is in the indicated operational state. Indicator components in accordance with embodiments of the invention broadly include visual, haptic and auditory indicators, each of which is described in further detail herein.

Aspects of the invention include visual indicator components that are configured or adapted to display a visual signal regarding an operational state of a subject system or device to a user. In some embodiments, a visual indicator comprises a light-emitting component. Light emitting components in accordance with embodiments of the invention include, without limitation, light emitting diodes (LEDs) and organic light emitting diodes (OLEDs). In some embodiments, a visual indicator comprises a light pipe (also referred to as a light tube). In some embodiments, a light pipe comprises a hollow structure that is configured to contain light within the structure by utilizing a reflective lining. In some embodiments, a light pipe comprises a transparent solid material that is configured to contain light within the material by utilizing total internal reflection. In some embodiments, a visual indicator comprises a diffuser component (e.g., a light pipe diffuser) that is configured to uniformly spread a visual signal (e.g., light from an LED) over a defined area. In some embodiments, a visual indicator component comprises a light pipe and a light pipe diffuser. Visual indicator components in accordance with embodiments of the invention can be configured or adapted to generate visual signals having any color (e.g., red, orange, yellow, green, blue, purple) or any combination thereof. In some embodiments, an operational state of a subject system or device can be assigned a specific color. For example, in one embodiment, an unready operational state is assigned the color red, and when the system or device is in an unready state, a red color is displayed to a user using a visual indicator component. In some embodiments, a visual indicator component can be configured to flash a visual indicator on and off in a particular sequence (e.g., a series of three short flashes) or to remain constantly on to provide an indication of an operational state.

Aspects of the invention include haptic indicator components that are configured or adapted to generate one or more vibration signals that are specific to an operational state of a subject system or device. In some embodiments, a haptic indicator comprises a vibration generator component. Vibration generator components in accordance with embodiments of the invention are configured or adapted to generate vibrations having any desired combination of amplitude, frequency and duration in order to generate a plurality of unique vibration signals. For example, in one embodiment, an unready operational state can be assigned a vibration signal that consists of a single, high amplitude vibration that has a duration of one second.

Aspects of the invention include auditory indicator components that are configured or adapted to generate one or more auditory signals that are specific to an operational state of a subject system or device. In some embodiments, an auditory indicator comprises a sound generator component. Sound generator components in accordance with embodiments of the invention are configured or adapted to generate a plurality of unique sounds having a plurality of different tones and/or volumes. For example, in one embodiment, an unready operational state can be assigned a sound that consists of a single, high-volume buzzer sound.

Indicator components in accordance with embodiments of the invention can be mounted in any suitable location on the subject systems or devices. For example, in some embodiments, an indicator component can be mounted in a housing that is positioned anywhere on the system or device. In some embodiments, an indicator component can comprise a plurality of individual components that work in concert to generate a desired indicator signal. For example, in one embodiment, a visual indicator component comprises an LED that generates a visible light signal, and also comprises a light pipe that transfers the visible light from the LED to one or more locations on the subject system or device. In some embodiments, a visual indicator further comprises a light pipe diffuser that evenly spreads the visible light signal over a desired location (e.g., over the entire area of a thumb pad, over an entire indicator window).

In one embodiment, an indicator component is mounted in a thumb pad that is attached to an actuation component (e.g., a syringe stopper rod, as described further herein). In some embodiments, an indicator component is configured to be removably coupled to subject drug delivery system or device. For example, in some embodiments, an indicator component is mounted in a thumb pad, and the thumb pad is configured to be removably coupled to a distal end of a syringe stopper rod.

Housing Component:

Aspects of the invention include one or more housing components that are formed from suitable materials, such as, e.g., glass, plastic, metal, or any combination thereof. In some embodiments, one or more individual components of the subject drug delivery systems or devices can be located within a single housing and formed into a single unit. In some embodiments, one or more components of the subject systems or devices can be located in a first housing component, and one or more additional components of the subject systems or devices can be located in a second housing component, and the first and second housing components can be operably coupled to one another to form a single unit.

In some embodiments, a housing comprises one or more transparent or semitransparent windows that are made of a material that is at least partially transparent to light, and is configured to allow ambient light to pass through the housing to reach a light sensor positioned therein. In some embodiments, a housing comprises one or more windows or openings that allow one or more components of the systems or devices to physically pass through.

FIGS. 1, 7, 8 and 10 depict drug delivery systems comprising a housing.

Drug Reservoir:

Aspects of the invention include a drug reservoir that is configured or adapted to contain a volume of a drug. In certain embodiments, a drug reservoir is operably coupled to one or more additional components of a subject system or device (e.g., an actuation component and/or a drug delivery cannula). In some embodiments, a drug can comprise a large or small molecule composition. In some embodiments, a drug can comprise a biological composition. Non-limiting examples of biological compositions include proteins (e.g., antibodies). In some embodiments, a drug can be in a fluid or liquid form, although the subject drug delivery systems and devices are not limited to a particular drug state. For example, in some embodiments, a drug reservoir can contain a liquid solution, a gel, or a solid (e.g., a lyophilized) drug substance. In some embodiments, a subject drug delivery system or device can comprise a plurality of drug reservoirs. In some embodiments, a first drug reservoir can contain, e.g., a lyophilized drug and a second drug reservoir can contain a liquid that can be used to reconstitute the lyophilized drug. In some embodiments, a subject drug delivery system or device is configured to carry out a mixing procedure, wherein a lyophilized drug is mixed with a reconstitution solution before the drug is administered to the patient.

Drug reservoirs in accordance with embodiments of the invention can be constructed from any suitable material, such as, e.g., glass, plastic, metal, or any combination thereof. In certain embodiments, a drug reservoir is configured or adapted to be non-reactive with a drug that is to be stored in the reservoir. In certain embodiments, a drug reservoir is configured to hold a volume of drug that ranges from about 10 μL up to about 1,000 mL, such as about 15, 20, 25, 30, 35, 40, 45, 50, 55, 60, 65, 70, 75, 80, 85, 90, 100, 125, 150, 200, 250, 300, 350, 400, 450, 500, 550, 600, 650, 700, 750, 800, 850, 900 or 950 μL or more, such as about 1, 5, 10, 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, or about 950 mL.

In some embodiments, a drug reservoir is configured or adapted to be stored at a variety of different temperatures. In some embodiments, a drug reservoir is configured to be stored at a temperature ranging from about −100 oc to about 40° C., such about −90, −80, −70, −60, −50, −40, −30, −20, −10, 0, 2-8, 10, 15, 20, 25, 30 or 35° C.

Drug reservoirs in accordance with embodiments of the invention are configured to maintain their contents in a sterile condition. In certain embodiments, a drug reservoir can comprise at least one sterile barrier that is configured to maintain the sterility of the reservoir's contents prior to use in a subject system or device, and is configured to be removed when the drug reservoir is operably coupled to a subject system or device. In some embodiments, a drug reservoir is configured to be removably coupled to one more components of a subject system or device (e.g., is configured to be removably coupled to an actuation component of a subject drug delivery device).

In some embodiments, a drug reservoir comprises a syringe, consisting of a stopper that fits tightly inside a syringe barrel. Movement of the stopper along the inside of the syringe barrel results in movement of a liquid that is present inside the syringe barrel. In some embodiments, a stopper is configured or adapted to be operably coupled to an actuation component (e.g., a syringe stopper rod) that is configured to move the stopper. In some embodiments, an end of the syringe that is opposite the stopper comprises an opening through which a liquid can be taken in or expelled, depending on the direction of motion of the stopper. In some embodiments, a syringe can be operably coupled to a drug delivery cannula (e.g., a needle or a catheter). In some embodiments, a drug delivery cannula can be removably coupled to a syringe. In some embodiments, a drug delivery cannula can be non-removably coupled to a syringe (e.g., a staked needle syringe). In some embodiments, a syringe is a pre-filled syringe, which contains a predetermined volume of liquid.

In some embodiments, a drug reservoir comprises a vial. Vials in accordance with embodiments of the invention are composed of any suitable material, e.g., glass, plastic, metal, or any combination thereof, and comprise one open end. In some embodiments, a vial comprises a removable cap that is configured to close the open end. In some embodiments, a cap comprises a stopper that is configured to be punctured, e.g., by a drug delivery cannula, or by one or more fluid coupler components that are configured to transfer the contents of the vial from one position to another within a subject system or device. In some embodiments, a stopper is a rubber stopper that is covered with a protective layer of metal to prevent accidental punctures of the stopper prior to use. FIG. 9, Panel B depicts one embodiment of a vial.

In some embodiments, a drug reservoir comprises a cartridge. Cartridges in accordance with embodiments of the invention are composed of any suitable material, e.g., glass, plastic, metal, or any combination thereof, and comprise one or more openings that are configured to operably couple to a subject drug delivery system or device. In some embodiments, a cartridge comprises a removable barrier that is configured to cover the one or more openings prior to use. FIG. 9, Panel A depicts one embodiment of a cartridge.

Aspects of the invention include a drug reservoir that comprises a memory component (as described herein) that is configured or adapted to store one or more drug identification characteristics. Memory components in accordance with embodiments of the invention can be volatile or non-volatile memory components. In certain embodiments, a sensor component is configured to acquire the one or more drug characteristics that are stored in the memory component on the drug reservoir. In some embodiments, a drug reservoir comprises a near-field communication (NFC) component and/or a radio frequency identification (RFID) component that are configured for data exchange.

FIGS. 1, 12 and 13 depict embodiments of drug delivery systems comprising a drug reservoir.

Drug Delivery Cannula:

Aspects of the invention include a drug delivery cannula that is configured to be inserted into a patient's body to deliver a medication. In some embodiments, a drug delivery cannula can comprise a rigid or semi-rigid needle. In some embodiments, a drug delivery cannula can comprise a catheter. Drug delivery cannulas in accordance with embodiments of the invention can be integrated with one or more components of the subject systems and devices, or can be separate components that are configured to be operably connected to a subject system or device for purposes of delivering a medication to a patient. In some embodiments, a drug delivery cannula can be configured for implantation into a patient, wherein at least a portion of the drug delivery cannula is configured or adapted to remain implanted in the patient (e.g., to remain placed in an artery or vein of a patient, or to remain placed under a patient's skin) for an extended period of time.

In certain embodiments, a drug delivery cannula can comprise one or more insertion components that are configured to introduce the drug delivery cannula into a desired position (e.g., into an artery or vein of a patient, or under a patient's skin) in order to carry out delivery of a medication. In some embodiments, an insertion component is configured to be removed before a medication is delivered to the patient, whereas in some embodiments, an insertion component is configured to remain in place while a medication is delivered to the patient. A non-limiting example of an insertion component is a catheter needle, which is configured to introduce a catheter into a patient's vein, and to be removed following placement of the catheter, leaving the catheter positioned in the vein.

In some embodiments, a subject drug delivery system or device comprises a drug delivery cannula shield (e.g., a needle shield) that is configured to protect a user from accidentally coming into contact with the drug delivery cannula. Drug delivery cannula shields in accordance with embodiments of the invention comprise an open proximal end, a closed distal end, and a tubular body having a length that is at least slightly longer than the drug delivery cannula prior to its deployment. In use, the drug delivery cannula shield is configured to be placed over the drug delivery cannula so that the open distal end mechanically interacts with one or more components of the drug delivery system or device (e.g., a distal end of a syringe barrel) to keep the drug delivery cannula shield in place until it is removed by a user. In certain embodiments, a drug delivery cannula shield is retractable, and is configured to retract when the shield is placed against a user's skin and pressure is applied. In some embodiments, after the drug has been delivered to the patient and pressure is removed from the system or device, the drug delivery cannula shield is configured to move back into position to protect the user from accidental contact with the drug delivery cannula. In some embodiments, a drug delivery cannula shield can comprise a spring mechanism that is configured to allow the shield to retract when pressure is applied, and to return to a protective position when pressure is removed.

Turning now to FIGS. 1, 10 and 13, drug delivery systems comprising a drug delivery cannula shield are depicted. In the drug delivery systems depicted in FIGS. 8 and 13, a drug delivery cannula is shown.

Needle Safety Device (Nsd):

Aspects of the invention include a needle safety device (NSD) that is configured or adapted to sequester the drug delivery cannula after it has been withdrawn from the patient. NSDs in accordance with embodiments of the invention include a housing component that is appropriately sized to sequester a drug delivery cannula. In some embodiments, an NSD is configured to be mechanically activated when the actuator component completes a delivery stroke. For example, in some embodiments, an NSD comprises one or more trigger elements that are triggered when the actuation component completes a delivery stroke. In some embodiments, an NSD comprises a trigger element that is triggered when one or more elements of the activation component makes contact with the trigger element, thereby configuring the NSD to be triggered when the activation component contacts the trigger element. In certain embodiments, an activation component comprises a contact switch with a predetermined force value required to activate the contact switch, and an NSD comprises a trigger element with a triggering force requirement that is higher than the predetermined force required to activate the contact switch. As such, a mechanical force that activates the NSD will necessarily activate the contact switch, thereby assuring that the sensor component is activated whenever the NSD is activated. In some embodiments, an NSD is activated simultaneously with activation of the sensor component. In some embodiments, an NSD is activated simultaneously with transmission of a report comprising a drug dose completion signal from the sensor component to the data management component.

In some embodiments, an NSD is configured to be electrically activated by a sensor component. For example, in some embodiments, when a sensor component is activated by an activation component at the completion of a delivery stroke, the sensor component sends an electronic activation signal to the NSD, causing the NSD to activate and sequester the drug delivery cannula.

In some embodiments, when the NSD is activated, the NSD changes position so that the drug delivery cannula is completely surrounded by (or sequestered within) the NSD component. In some embodiments, an NSD is configured to move over a drug delivery cannula. In some embodiments, a drug delivery cannula is configured to move within an NSD. In some embodiments, an NSD is configured to lock into place to sequester the drug delivery cannula inside the NSD when the NSD is activated. This prevents a user from accidentally coming into contact with drug delivery cannula after it has been used.

Figure 7:
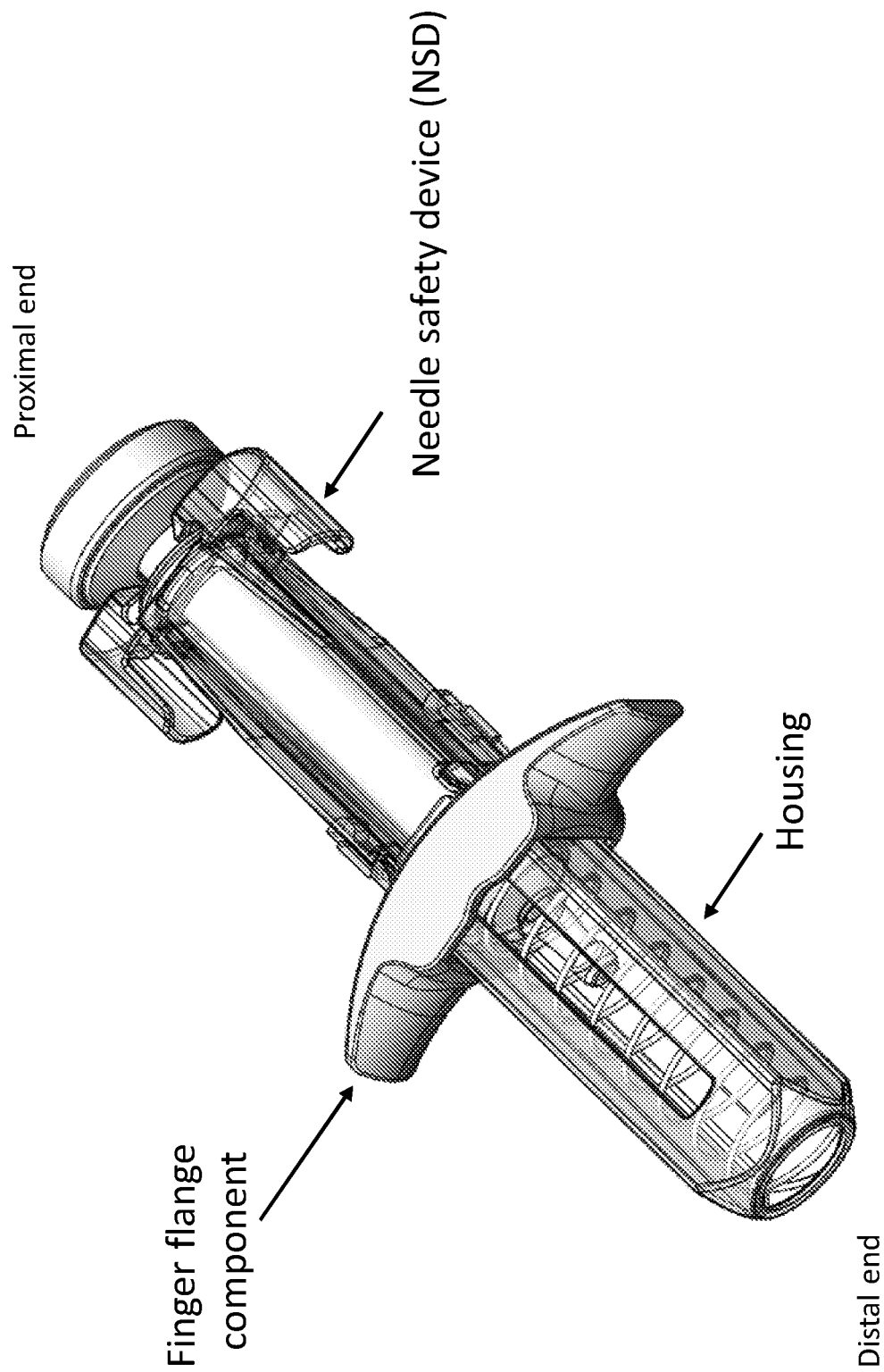
FIG. 7 is a three dimensional rendering of a drug delivery system according to one embodiment of the invention.

Turning now to FIG. 7, a drug delivery system comprising an NSD is depicted. In the depicted embodiment, the NSD is in an activated state, and is extended over the drug delivery cannula to sequester the drug delivery cannula. In FIG. 8, the same drug delivery system is depicted prior to activation of the NSD. As depicted, the drug delivery system in FIG. 8 comprises a drug delivery cannula that has not yet been sequestered within the NSD. Further depicted in FIG. 8 is an NSD triggering element that is configured to trigger the NSD when the syringe stopper rod mechanically interacts the NSD triggering element. FIGS. 10, 12 and 13 depict additional embodiments of drug delivery systems comprising NSDs with triggering elements.

Finger Flange Component:

Aspects of the invention include a finger flange component that is configured or adapted to be coupled to a subject system or device (e.g., configured to be coupled to a housing of a subject device, or to be coupled to a syringe barrel of a subject device). Finger flange components in accordance with embodiments of the invention comprise lateral surfaces that increase the surface area available for a user's fingers to grasp a subject device. The additional surface area makes it easier for a user to grip and control the device during administration of the drug.

In some embodiments, a finger flange component is configured to be removably coupled to a subject system or device. For example, in some embodiments, a finger flange component is configured to be press fitted onto a housing, or onto a drug reservoir (e.g., onto a pre-filled syringe) and can comprise one or more mechanical components (e.g., snap components) that can mate with one or more complementary components on, e.g., a housing or a drug reservoir, in order to ensure a secure connection. In some embodiments, a finger flange component can be integrated with a needle safety device (NSD) as described above. In some embodiments, a sensor component is configured to fit within a finger flange component. In certain embodiments, a sensor component comprises two or more individual units, and each unit is configured to fit on one side of a finger flange component, so that a first unit of the sensor component is located on a first side of a finger flange component, and a second unit of the sensor component is located on a second side of the finger flange component.

Turning now to FIG. 1, a drug delivery system comprising a finger flange component is depicted. Further embodiments that comprise finger flange components are depicted in FIGS. 7, 8, 10, 12 and 13.

Data Management Component:

Aspects of the invention include a data management component that is configured or adapted to communicate with the subject systems or devices and/or a user, e.g., to receive a report comprising a drug dose completion signal from a subject system or device, to send one or more commands to a subject system or device, or to send a reminder to a user that a drug dose is due to be administered at a certain time. In some embodiments, a data management component comprises a computer (e.g., a personal computer, a networked computer or a network server). In some embodiments, a data management device comprises a mobile computing device (e.g., a smart phone, or a laptop computer). In some embodiments, a data management component is an Internet-enabled device that is capable of sending and receiving information over the Internet. In some embodiments, a data management component comprises an application that is configured to manage one or more aspects relating to administration of a drug to a user (e.g., to record administration of individual drug doses to a patient, to remind a patient regarding upcoming drug dose administrations, to validate one or more drug identification characteristics by interacting with a remote database, etc.). In some embodiments, a data management component is configured to indicate to a user that one or more communication components are operational and/or are connected to one or more additional components of the subject drug delivery systems or devices. For example, in some embodiments, a data management component is configured to indicate to a user that the data management component is connected (e.g., via a Bluetooth or WiFi connection) to a subject drug delivery system or device. In some embodiments, one or more indicator components on a subject drug delivery system or device, as described above, can further be used to indicate to a user that the data management component is connected to the system or device. Any suitable combination of indicator components on the data management component and/or the other components of the system or device can be used to indicate a connection status of the data management component to a user (e.g., connected, attempting to connect, not connected, disconnected, etc.).

In some embodiments, a data management component is configured or adapted to receive a report from a subject drug delivery system or device, and to record one or more aspects of the report for purposes of maintaining a patient's medical record/history. For example, in some embodiments, a data management component is configured to receive a report from a system or device that indicates a drug dose was administered to the patient, and the data management component records administration of the drug dose, including the date and time at which the drug dose was delivered. In some embodiments, a report can contain additional information relating to, e.g., the drug that was administered or the patient that received the drug. In some embodiments, a report can contain information relating to one or more operational states of the subject systems or devices. For example, in some embodiments, a report comprises information relating to, e.g., the temperature or temperature history of a system or device. In some embodiments, a report comprises information relating to a geographical location of the drug delivery system at the time of administration. In some embodiments, a report comprises information relating to an anatomical location on a patient's body (e.g., the patient's right arm, or the patient's left leg) where the dose was delivered.

In some embodiments, a data management component is configured or adapted to receive one or more data inputs from a subject system or device, and to validate the one or more data inputs prior to proceeding with administration of the drug to the patient. For example, in some embodiments, a data management component is configured to receive a drug identification characteristic from a subject system or device (e.g., from a drug reservoir that has been coupled to the system or device), and to verify that the drug identification characteristic is valid before proceeding with administration of the drug to the patient. In some embodiments, a data management component is configured to transmit one or more drug identification characteristics over the Internet to a remote database, and to receive an authentication signal in response, prior to administering the drug to the patient.

In some embodiments, a data management component is configured or adapted to determine whether a specific drug delivery system or device, or a component thereof (e.g., a drug reservoir) is the result of an authorized sale from a manufacturer, and/or an authorized prescription of the drug from a prescribing health care provider (e.g., from a prescribing physician), in a specific geographical location (e.g., in a specific country). For example, in some embodiments, a data management component is configured to receive one or more drug identification characteristics from a subject drug delivery system or device (or a component thereof, e.g., a drug reservoir), and to transmit the one or more drug identification characteristics to a remote database. In some embodiments, a data management component is further configured or adapted to transmit a geographical location of the drug delivery system or device to the remote database as well. In some embodiments, a remote database is configured or adapted to compare the one or more drug identification characteristics with the geographical location received from the data management component to determine whether a specific drug delivery system or device, or component thereof (e.g., a drug reservoir), is being used in the geographical location (e.g., the specific country) where it was sold.

In some embodiments, a data management component is configured to validate one or more operational states of the subject systems or devices prior to administration of the drug to the patient. For example, in one embodiment, a data management component is configured to determine whether a drug reservoir is at a temperature that falls within a predetermined acceptable temperature range prior to administering the drug to the patient. In some embodiments, a data management component is configured to verify that a subject system or device is in a "ready" operational state prior to administering the drug to the patient.

Data management components in accordance with embodiments of the invention are configured to determine a date and time at which a drug is administered to a patient (e.g., a time stamp for the drug dose administration). In some embodiments, a data management component is configured to receive a drug dose completion signal from a subject system or device, and is configured to determine the exact time of the drug administration based on additional information transmitted from the system or device. For example, in some situations, a subject system or device may not be operatively connected to a data management component at the specific date and time at which administration of the drug was carried out. In such instances, a subject system or device is configured to determine an elapsed time since completion of the drug administration procedure. When the system or device becomes connected to the data management component, a drug dose delivery signal as well as the elapsed time since the administration is transmitted to the data management component. The data management component then utilizes the transmitted information to back-calculate the specific date and time at which the drug administration procedure was completed, and records this information in the patient's records.

In some embodiments, a subject system or device can comprise a controller, a processor, and a computer readable medium that are configured or adapted to control or operate one or more components of the subject systems or devices. In some embodiments, a system or device includes a controller that is in communication with one or more components of the subject systems of devices, and is configured to control aspects of the systems or devices and/or execute one or more operations or functions of the subject systems or devices. In some embodiments, a system or device includes a processor and a computer-readable medium, which can include memory media and/or storage media. Applications and/or operating systems embodied as computer-readable instructions on the computer-readable memory can be executed by the processor to provide some or all of the functionalities described herein.

In some embodiments, a subject system or device includes a user interface, such as a graphical user interface (GUI), that is configured or adapted to receive an input from a user, and to execute one or more of the methods as described further herein. In some embodiments, a GUI is configured to display data or information to a user.

Preferred Embodiments

In a first preferred embodiment, an actuation component comprises a syringe stopper rod having a distal end and a proximal end, and comprising a hollow, elongated rod element that extends from the distal end to the proximal end. At the distal end, the syringe stopper rod comprises a threaded coupling component that is configured to screw into a syringe stopper. Inside the elongated rod element there is a light pipe and a light pipe diffuser. The light pipe has an elongated shape, and its proximal end is located adjacent to a visual indicator component comprising an LED. The proximal end of the syringe stopper rod comprises a sensor housing, in which is located a sensor component comprising a PCBA, a visual indicator component, a momentary contact switch, and a battery. The sensor housing further comprises a thumb pad located on its proximal face. The thumb pad is removably coupled to the sensor housing to allow access to the sensor component.

The sensor housing of the first preferred embodiment comprises a plurality of openings that allow an activation component to mechanically interact with the momentary contact switch on the sensor component by passing through the sensor housing. The activation component comprises an activation cam that is mounted on the elongated rod element and that is located on an external distal face of the sensor housing. The activation component further comprises a switch key that is mounted on the elongated rod element and that is located on an internal distal face of the sensor housing. The activation cam comprises a plurality of extension tabs that pass through the openings in the sensor housing to contact switch key when the activation cam is activated.

In use, the syringe stopper rod of the first preferred embodiment is connected to a component of a drug reservoir, e.g., a syringe stopper of a pre-filled syringe, and serves as part of an actuation component. The drug delivery system further comprises a housing that surrounds the drug reservoir, a drug delivery cannula, a needle shield, a needle safety device, and a finger flange component. A user then inserts the drug delivery cannula into an appropriate position (e.g., inserts a needle that is operably attached to the syringe under a patient's skin) and then applies a force to the proximal end of the syringe stopper rod, causing the syringe stopper to move in the distal direction and to dispense the drug from the reservoir through the drug delivery cannula and into the patient. When the sensor housing reaches the distal end of the syringe, the delivery stroke is complete. Upon completion of the delivery stroke, the activation cam abuts the distal end of the syringe and the extension tabs of the activation cam exert a force on the switch key, causing it to activate the momentary switch on the sensor component. Activation of the momentary switch triggers the sensor component to transmit a report comprising a drug dose completion signal to the data management component, indicating that the drug dose has been administered to the patient. The data management system records the drug dose administration information in the patient's record. Following administration of the drug dose, the syringe stopper rod can be unscrewed from the syringe and kept for subsequent use, while the used syringe and drug delivery cannula can be disposed of using appropriate biohazard waste disposal procedures. The first preferred embodiment is depicted in FIGS. 2-6.

In a second preferred embodiment, an actuation component comprises a syringe stopper rod having a distal end and a proximal end, and comprising a hollow, elongated external rod element that extends from a position near the distal end to the proximal end. The actuation component further comprises an elongated internal rod element that extends from the distal end to a position near the proximal end, directly adjacent to a momentary switch on a distal face of the sensor component. At its distal end, the external rod element comprises one or more detent snaps. At a position located just proximal to its distal end, the internal rod element comprises a plurality of detent snap depressions. At the distal end, the internal rod element comprises a threaded coupling component that is configured to screw into a syringe stopper.

The proximal end of the syringe stopper rod comprises a sensor housing, in which is located a sensor component comprising a PCBA, a momentary contact switch, and a battery. The sensor housing further comprises a thumb pad located on its proximal face. The thumb pad is removably coupled to the sensor housing to allow access to the sensor component.

In use, the syringe stopper rod of the second preferred embodiment is connected to a component of a drug reservoir, e.g., a syringe stopper of a pre-filled syringe, and serves as part of an actuation component. The drug delivery system further comprises a housing that surrounds the drug reservoir, a drug delivery cannula, a needle shield, a needle safety device, and a finger flange component. A user then inserts the drug delivery cannula into an appropriate position (e.g., inserts a needle that is operably attached to the syringe under a patient's skin) and then applies a force to the proximal end of the syringe stopper rod, causing the syringe stopper to move in the distal direction and to dispense the drug from the reservoir through the drug delivery cannula and into the patient. When the syringe stopper reaches the distal end of the syringe, the delivery stroke is complete. Upon completion of the delivery stroke, the external rod element exerts a force on the detent snaps, causing them to shift from a more proximal detent snap depression to a more distal detent snap depression, thereby causing the internal rod element to move in the proximal direction with respect to the external rod element. This motion causes the internal rod element to activate the momentary switch on the sensor component.

Activation of the momentary switch triggers the sensor component to transmit a report comprising a drug dose completion signal to the data management component, indicating that the drug dose has been administered to the patient. The data management system records the drug dose administration information in the patient's record. Following administration of the drug dose, the syringe stopper rod can be unscrewed from the syringe and kept for subsequent use, while the used syringe and drug delivery cannula can be disposed of using appropriate biohazard waste disposal procedures. The second preferred embodiment is depicted in FIGS. 11-13.

In a third preferred embodiment, a drug delivery system comprises an actuation component comprising a syringe stopper and an associated rod element having a distal end and a proximal end. The drug delivery system further comprises a pre-filled syringe, a housing, a needle safety device (NSD) comprising two trigger elements located on each side of the NSD, a needle, a needle shield, and a finger flange component. The finger flange component comprises a sensor housing, in which is located a sensor component that comprises two separate units, each unit comprising a PCBA. The first sensor unit comprises a battery, and the second sensor unit comprises a visual indicator component, a wireless transmitter module, a memory component, and an activation component. The first and second sensor units are electrically coupled to one another. The finger flange component is removably coupled to the housing of the drug delivery system. The activation component is located on a proximal face of the finger flange component, and is configured to be activated when the proximal end of the syringe stopper rod mechanically contacts the NSD trigger elements and activates the NSD.

In use, a user removes the needle shield and inserts the needle into an appropriate position (e.g., inserts the needle under a patient's skin), and then applies a force to the proximal end of the syringe stopper rod, causing the syringe stopper to move in the distal direction and to dispense the drug from the drug reservoir through the needle and into the patient. When the syringe stopper reaches the distal end of the syringe, the delivery stroke is complete. Upon completion of the delivery stroke, the proximal end of the syringe stopper rod mechanically contacts the trigger elements of the NSD, thereby triggering the NSD and causing it to sequester the needle. Triggering the NSD also activates the activation component, which triggers the sensor component to transmit a report comprising a drug dose completion signal to the data management component, indicating that the drug dose has been administered to the patient. The data management system records the drug dose administration information in the patient's record (e.g., in a computer application that is installed on the data management component). Following administration of the drug dose, the finger flange component can be removed from the system and kept for subsequent use, while the used syringe and drug delivery cannula can be disposed of using appropriate biohazard waste disposal procedures. The third preferred embodiment is depicted in FIGS. 7, 8 and 10.

Methods of Use:

Aspects of the invention include methods for operating the subject drug delivery systems and devices to deliver a drug dose to a patient, and to record information relating to the drug dose administration in a data management component. In some embodiments, the subject methods comprise verifying one or more operational states of a subject system or device prior to administering the drug dose to the patient. In some embodiments, the subject methods comprise authenticating a drug in a subject system or device prior to administering the drug to the patient.

In one embodiment, a subject method comprises inserting a drug delivery cannula of a subject drug delivery system into a patient and completing a delivery stroke of the actuation component, thereby causing the activation component to activate the sensor component, causing a wireless transmitter module in the sensor component to transmit a report comprising a drug dose completion signal to the data management system. Upon receipt of the report, the data management system records administration of the drug dose to the patient. By automating this step, the user is ensured of more accurate record keeping regarding administration of the drug. In addition, other parties, such as a treating physician or health care network, can have greater access to more accurate information regarding the patient's medical record, e.g., the history of administration of the drug.

In some embodiments, the subject methods comprise a validation or verification step in which one or more data values are received from the subject drug delivery systems or devices, and are validated or verified to determine whether the drug is suitable for administration to the a patient. In some embodiments, the subject methods comprise verification of one or more drug identification characteristics, e.g., a drug identification number, in order to confirm the authenticity of the drug. In some embodiments, the subject methods comprise analyzing a plurality of data collected from the sensor component of a subject drug delivery system or device to evaluate one or more environmental parameters. For example, in one embodiment, the subject methods comprise analyzing the temperature history of a drug reservoir to verify that the drug reservoir has been maintained under required temperature conditions prior to administration of the drug to the patient. By including a sensor component on the subject systems and devices, many of the steps associated with verifying the authenticity and condition of a given drug can be done automatically using a data management component, providing greater case of use to the end user, and providing more accurate safety and administration information.

In some embodiments, the subject methods comprise utilizing a computer application (e.g., a mobile application) on a subject data management component that is configured or adapted to facilitate improved patient adherence to a drug dosage regimen by recording the date and time of each administration of a drug to the patient. In some embodiments, the methods involve recording the date and time of each administration of a drug dose to the patient so that the patient can be accurately reminded when the next administration of the drug dose should take place in accordance with a prescribed drug dose regimen. In some embodiments, the subject methods involve sending a reminder to a patient that a drug dose is due to be administered at a designated time. For example, in some embodiments, the subject methods involve sending one or more regularly-scheduled reminders to the patient to administer a dose of a drug. In some embodiments, the subject methods comprise sending a reminder to the patient at a predetermined time, e.g., every day at a specific time. In some embodiments, the subject methods involve determining when a subsequent dose of a drug is due to be administered to a patient based on the patient's prior administrations of the drug, and sending a reminder to the patient at a predetermined time, (e.g., about 1 hour, about 30 minutes, or about 10 minutes) before the drug dose is due to be administered. In some embodiments, the subject methods involve monitoring a patient's adherence to a drug dosage regimen, and sending a notification to one or more third parties if the patient is not adequately adhering to the dosage regimen. For example, in some embodiments, the subject methods comprise sending a notification to one or more members of a patient's family if the patient is not adhering to the dosage regimen. In some embodiments, the subject methods comprise sending a notification to one or more health care providers (e.g., to a prescribing physician) if the patient is not adhering to a dosage regimen.

Aspects of the invention include Internet-based computing techniques (also known as "cloud computing" techniques) that involve sending and/or receiving information to or from one or more shared computer processing resources and/or data repositories over the Internet at the time such resources are needed or used by a user. Such techniques allow a user to utilize sophisticated computing equipment without being required to personally purchase and maintain the equipment. In addition, Internet-based computing techniques facilitate access to user information by patient-authorized third parties, such as, e.g., health care providers, or drug manufacturers.

In some embodiments, the subject methods comprise sending one or more drug identification characteristics to a remote database, and receiving, in response, one or more additional drug identification characteristics that can be recorded by the data management system. For example, in one embodiment, the subject methods comprise receiving a first drug identification characteristic (e.g., a drug lot number) from a subject system or device, and transmitting the first drug identification characteristic to a remote database using the data management component. The remote database uses the first drug identification characteristic to retrieve one or more additional drug identification characteristics, which are then transmitted back to the data management component.

Aspects of the invention relate to methods for monitoring the progress of a clinical trial. In some embodiments, the subject drug delivery systems and devices can be used to electronically track one or more individual patients in a clinical trial, and to record one or more items of information associated with each administration of a drug. For example, in some embodiments, the subject drug delivery systems and devices can be used to monitor the progress of a clinical trial while providing adequate protection of the rights of any human subjects involved the clinical trial by rendering the data anonymous to any personnel who are administering the trial. The subject systems and devices can be used to transmit and/or store information relating to successful administration of a drug dose to a patient, and the information can be reviewed by personnel administering the clinical trial to monitor the progress of the clinical trial. In some embodiments, the subject systems and devices can be used to record one or more drug identification characteristics, such as, e.g., a drug lot number, for each patient in a clinical trial. At any point during the progress of the trial, and/or at the completion of the trial, the drug identification information can be used to analyze the results of the trial, e.g., to determine patient response as a function of one or more drug identification characteristics.

In some embodiments, the subject methods result in improved patient adherence to a drug dosage regimen. For example, in some embodiments, implementation of the subject methods, as described above, results in an increase in patient adherence to a drug dosage regimen by an amount that ranges from about 1% up to about 75% or more, such as about 2%, 3%, 4%, 5%, 6%, 7%, 8%, 9%, 10%, 15%, 20%, 25%, 30%, 35%, 40%, 45%, 50%, 55%, 60%, 65%, or about 70% or more.

In some embodiments, the subject methods comprise separating one or more components of the subject systems and devices following administration of the drug to the patient, and separately disposing of the individual components. For example, in one embodiment, a portion of a subject system or device that comprises electronic components (e.g., a circuit board component, a power component, etc.) can be separated from the remainder of the device and disposed of according to electronic waste handling procedures. Separation of the electronic components from the remainder of the device reduces the amount of electronic waste, as the non-electronic components (e.g., the housing, the drug reservoir, etc.) can be disposed of separately.

Similarly, in some embodiments, a portion of the subject system or device that comprises biohazard waste (e.g., a drug delivery cannula, a drug reservoir, etc.) can be separated from the remainder of the device and disposed of according to biohazard waste handling procedures. Separation of the biohazard waste from the remainder of the device reduces the amount of biohazard waste, as the non-biohazardous components (e.g., the electronic components) can be disposed of separately.

What is claimed is:

1. A syringe stopper rod comprising:
a rod portion having a proximal end and a distal end;
a stopper located at the distal end of the rod portion;
a thumb pad located at the proximal end of the rod portion; and
an activation component located adjacent to the thumb pad,
wherein the stopper and the rod portion are configured to be received within a barrel of a syringe during use and the thumb pad is configured to manually drive the stopper and rod portion distally into the syringe barrel,
wherein the thumb pad includes a sensor component comprising:
a battery;
a printed circuit board assembly; and
a wireless transmitter module,
wherein the entire sensor component resides on the thumb pad,
wherein the activation component is configured to activate the sensor component when the syringe stopper rod has completed a delivery stroke in a syringe barrel,
wherein the wireless transmitter module is configured to transmit a report comprising a drug dose completion signal when the sensor component is activated.

2. A syringe system comprising:
the syringe stopper rod according to claim 1; and
a syringe barrel.

3. The syringe system according to claim 2, wherein the syringe barrel is pre-filled with a medication before being sold to a consumer.

4. The syringe system according to claim 2, further comprising a needle coupled to a distal end of the syringe barrel.

5. The syringe system according to claim 4, wherein the syringe barrel comprises a needle safety device configured to sequester the needle upon completion of a delivery stroke of the syringe stopper rod in the syringe barrel.

6. A drug delivery system comprising:
the syringe system according to claim 2; and
a data management system configured to receive and record the report from the sensor component.

7. The drug delivery system according to claim 6, wherein the drug delivery system further comprises a nonvolatile memory component that is encoded with at least one drug identification characteristic.

8. The drug delivery system according to claim 6, wherein the nonvolatile memory component is located within the thumb pad.

9. The drug delivery system according to claim 6, wherein the data management system comprises a smart phone having a computer application configured to record administration of a drug dose to a patient.

10. The drug delivery system according to claim 6, wherein the report comprises at least one item selected from the group consisting of a drug temperature value, a dose amount, a dose administration time stamp, a geographical location, an anatomical location, and a drug authentication signal.

11. The drug delivery system according to claim 6, wherein the report comprises a drug authentication signal and wherein the drug authentication signal comprises at least one drug identification characteristic selected from the group consisting of a drug name, a drug concentration, a drug dose, a drug dosage, a serial number, a lot number, an expiration date and a manufacturing site.

12. The drug delivery system according to claim 6, wherein the report comprises a drug authentication signal and wherein the data management system is configured to validate the drug authentication signal.

13. The drug delivery system according to claim 6, wherein the report comprises a drug authentication signal and wherein the data management system is configured to utilize the drug authentication signal to obtain one or more additional drug identification characteristics.

14. The drug delivery system according to claim 13, wherein the data management system is configured to transmit the drug authentication signal to a remote database and receive the one or more additional drug identification characteristics in response.

15. A method for recording administration of a drug dose to a patient, the method comprising:
inserting the needle of the drug delivery system according to claim 6 into the patient;
completing a delivery stroke of the syringe stopper rod, thereby causing the activation component to activate the sensor component, and causing the wireless transmitter module to transmit a report comprising a drug dose completion signal to the data management system; and
receiving and recording the report in the data management system, thereby recording administration of the drug dose to the patient.

16. The method for recording administration of a drug dose to a patient according to claim 15, further comprising:
transmitting a drug authentication signal in the report transmitted by the wireless transmitter module to the data management system; and
validating the drug authentication signal with the data management system.

17. The method for recording administration of a drug dose to a patient according to claim 15, further comprising:
transmitting a drug authentication signal in the report transmitted by the wireless transmitter module to the data management system; and
utilizing the drug authentication signal with the data management system to obtain one or more additional drug identification characteristics.

18. The method for recording administration of a drug dose to a patient according to claim 17, further comprising:
transmitting the drug authentication signal from the data management system to a remote database; and
receiving the one or more additional drug identification characteristics in response.

19. The syringe system according to claim 2, further comprising an indicator component.

20. The syringe system according to claim 19, wherein the indicator component is configured to indicate at least one state to a user, the at least one state selected from the group consisting of a ready state, an unready state, a dose-in-progress state, a dose completed state, a sleep mode and a low battery state.

21. The syringe system according to claim 20, wherein the indicator component comprises at least one component selected from the group consisting of a visual indicator component, a haptic indicator component and an auditory indicator component.

22. The syringe system according to claim 21, wherein the indicator component comprises at least one visual indicator component selected from the group consisting of a light-emitting component, a light emitting diode (LED), an organic light-emitting diode (OLED), a light pipe and a light pipe diffuser.

23. The syringe system according to claim 21, wherein the indicator component comprises a haptic indicator component that includes a vibration component.

24. The syringe system according to claim 2, wherein the sensor component comprises a non-volatile memory component and the non-volatile memory component comprises at least one drug identification characteristic.

25. The syringe system according to claim 24, wherein the at least one drug identification characteristic is selected from the group consisting of a drug name, a drug concentration, a drug dose, a drug dosage, a serial number, a lot number, an expiration date and a manufacturing site.

* * * * *